(12) United States Patent
Dickson et al.

(10) Patent No.: US 10,662,431 B2
(45) Date of Patent: May 26, 2020

(54) OLIGOMERS

(71) Applicant: Royal Holloway and Bedford New College, Surrey (GB)

(72) Inventors: John George Dickson, London (GB); Jagjeet Kaur Kang, Surrey (GB)

(73) Assignee: ROYAL HOLLOWAY AND BEDFORD NEW COLLEGE, Surrey (GB)

(*) Notice: Subject to any disclaimer, the term of this patent is extended or adjusted under 35 U.S.C. 154(b) by 0 days.

(21) Appl. No.: 16/539,732

(22) Filed: Aug. 13, 2019

(65) Prior Publication Data
US 2020/0017859 A1 Jan. 16, 2020

Related U.S. Application Data

(60) Continuation of application No. 16/129,680, filed on Sep. 12, 2018, now Pat. No. 10,421,969, which is a continuation of application No. 15/078,029, filed on Mar. 23, 2016, now Pat. No. 10,106,795, which is a division of application No. 14/504,453, filed on Oct. 2, 2014, now Pat. No. 9,322,019, which is a continuation of application No. 13/644,363, filed on Oct. 4, 2012, now abandoned.

(60) Provisional application No. 61/543,145, filed on Oct. 4, 2011.

(51) Int. Cl.
*C07H 21/04* (2006.01)
*C12N 15/113* (2010.01)
*A61K 47/54* (2017.01)

(52) U.S. Cl.
CPC .......... *C12N 15/1136* (2013.01); *A61K 47/54* (2017.08); *C07H 21/04* (2013.01); *C12N 15/1138* (2013.01); *C12N 2310/11* (2013.01); *C12N 2310/314* (2013.01); *C12N 2310/321* (2013.01); *C12N 2310/3233* (2013.01); *C12N 2320/30* (2013.01); *C12N 2320/31* (2013.01); *C12N 2320/33* (2013.01)

(58) Field of Classification Search
None
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 5,013,556 A | 5/1991 | Woodle et al. |
| 5,034,506 A | 7/1991 | Summerton et al. |
| 5,108,921 A | 4/1992 | Low et al. |
| 5,142,047 A | 8/1992 | Summerton et al. |
| 5,166,315 A | 11/1992 | Summerton et al. |
| 5,185,444 A | 2/1993 | Summerton |
| 5,213,804 A | 5/1993 | Martin et al. |
| 5,217,866 A | 6/1993 | Summerton et al. |
| 5,227,170 A | 7/1993 | Sullivan |
| 5,264,221 A | 11/1993 | Tagawa et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,506,337 A | 4/1996 | Summerton et al. |
| 5,512,295 A | 4/1996 | Kornberg et al. |
| 5,521,063 A | 5/1996 | Summerton et al. |
| 5,521,291 A | 5/1996 | Curiel et al. |
| 5,527,528 A | 6/1996 | Allen et al. |
| 5,534,259 A | 7/1996 | Zalipsky et al. |
| 5,539,082 A | 7/1996 | Nielsen et al. |
| 5,543,152 A | 8/1996 | Webb et al. |
| 5,543,158 A | 8/1996 | Gref et al. |
| 5,547,932 A | 8/1996 | Curiel et al. |

(Continued)

FOREIGN PATENT DOCUMENTS

| | | |
|---|---|---|
| AU | 2015203791 | 10/2017 |
| CN | 108699555 | 10/2018 |

(Continued)

OTHER PUBLICATIONS

USPTO; Restriction Requirement dated Mar. 17, 2008 in U.S. Appl. No. 11/433,724.
USPTO; Non-Final Office Action dated Sep. 17, 2008 in U.S. Appl. No. 11/433,724.
USPTO; Non-Final Office Action dated Jun. 11, 2009 in U.S. Appl. No. 11/433,724.
USPTO; Final Office Action dated Mar. 10, 2010 in U.S. Appl. No. 11/433,724.

(Continued)

Primary Examiner — Kimberly Chong
(74) Attorney, Agent, or Firm — Snell & Wilmer LLP

(57) ABSTRACT

Certain disclosed oligomers induce exon skipping during processing of myostatin pre-mRNA. The oligomers may be in a vector or encoded by the vector. The vector is used for inducing exon skipping during processing of myostatin pre-mRNA. A therapeutically effective amount of the oligomer may be administered to a subject patient such that exon skipping during processing of myostatin pre-mRNA is induced. The administration to a subject may be used in order to increase or maintain muscle mass, or slowing degeneration of muscle mass in the subject. The administration to a subject may ameliorate muscle wasting conditions, such as muscular dystrophy. Examples of such muscular dystrophies which may be so treated include Becker's muscular dystrophy, congenital muscular dystrophy, Duchenne muscular dystrophy, distal muscular dystrophy, Emery-Dreifuss muscular dystrophy, facioscapulohumeral muscular dystrophy (FSHD), limb-girdle muscular dystrophy, myotonic muscular dystrophy, and oculopharyngeal muscular dystrophy.

Figures 1A, 1B:
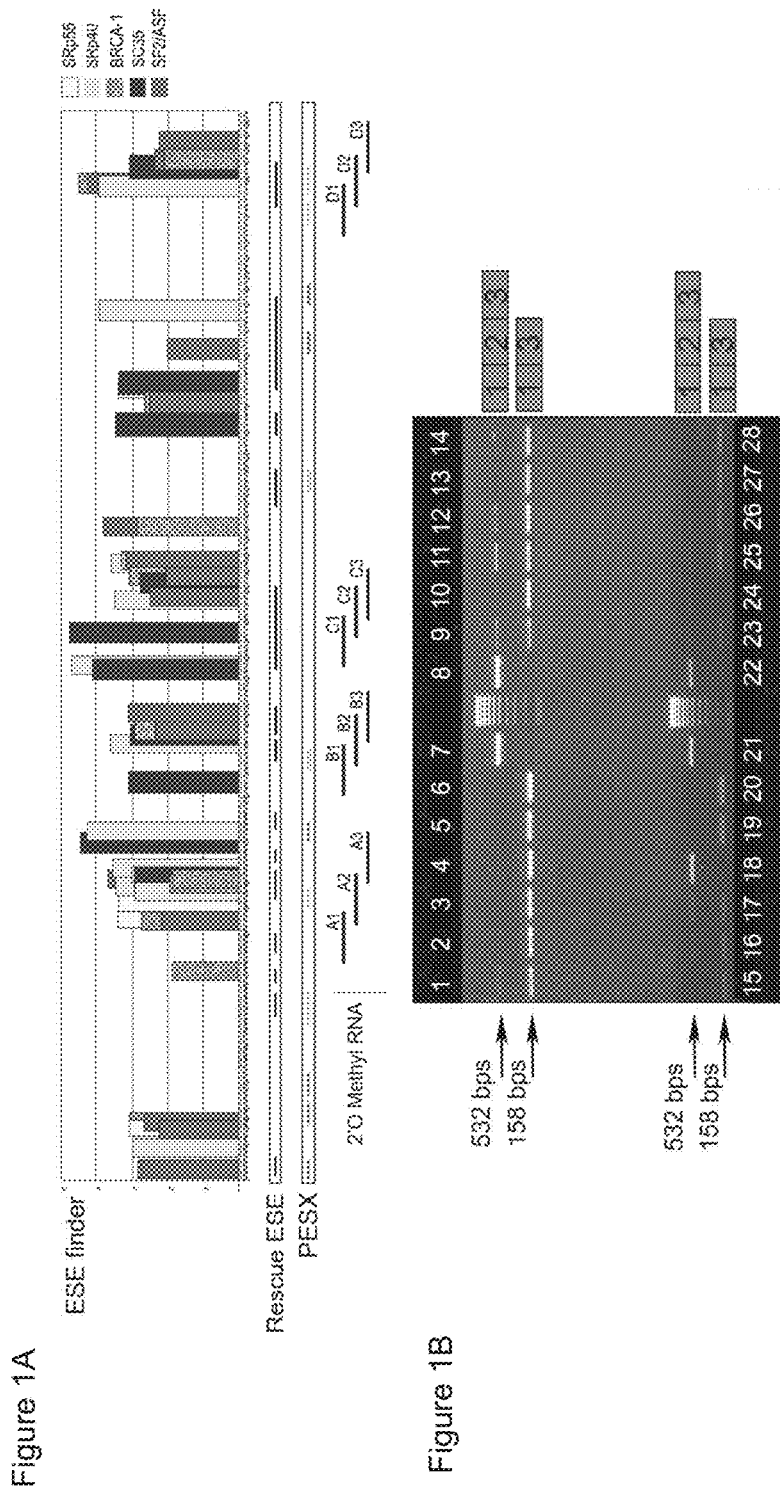

18 Claims, 4 Drawing Sheets
Specification includes a Sequence Listing.

(56) References Cited

U.S. PATENT DOCUMENTS

| | | |
|---|---|---|
| 5,556,948 A | 9/1996 | Tagawa et al. |
| 5,580,575 A | 12/1996 | Unger et al. |
| 5,583,020 A | 12/1996 | Sullivan |
| 5,591,721 A | 1/1997 | Agrawal et al. |
| 5,595,756 A | 1/1997 | Bally et al. |
| 5,627,274 A | 5/1997 | Kole et al. |
| 5,665,593 A | 9/1997 | Kole et al. |
| 5,698,685 A | 12/1997 | Summerton et al. |
| 5,707,618 A | 1/1998 | Armentano et al. |
| 5,714,331 A | 2/1998 | Buchardt et al. |
| 5,719,262 A | 2/1998 | Buchardt et al. |
| 5,770,713 A | 6/1998 | Imbach et al. |
| 5,916,808 A | 6/1999 | Kole et al. |
| 5,976,879 A | 11/1999 | Kole et al. |
| 6,005,079 A | 12/1999 | Casterman et al. |
| 6,060,456 A | 5/2000 | Arnold et al. |
| 6,096,506 A | 8/2000 | Lee et al. |
| 6,103,466 A | 8/2000 | Grobet et al. |
| 6,133,246 A | 10/2000 | McKay et al. |
| 6,172,216 B1 | 1/2001 | Bennnett et al. |
| 6,210,892 B1 | 4/2001 | Bennnett et al. |
| 6,214,986 B1 | 4/2001 | Bennnett et al. |
| 6,228,579 B1 | 5/2001 | Zyskind et al. |
| 6,239,265 B1 | 5/2001 | Cook |
| 6,245,747 B1 | 6/2001 | Porter et al. |
| 6,284,882 B1 | 9/2001 | Wu Wong et al. |
| 6,287,860 B1 | 9/2001 | Monia et al. |
| 6,365,351 B1 | 4/2002 | Iversen |
| 6,399,312 B2 | 6/2002 | Wu-Wong et al. |
| 6,468,535 B1 | 10/2002 | Lee et al. |
| 6,495,663 B1 | 12/2002 | Rothbard et al. |
| 6,617,440 B1 | 9/2003 | Findly |
| 6,653,467 B1 | 11/2003 | Matsuo et al. |
| 6,669,951 B2 | 12/2003 | Rothbard et al. |
| 6,670,461 B1 | 12/2003 | Wengel et al. |
| 6,677,153 B2 | 1/2004 | Iversen |
| 6,784,291 B2 | 8/2004 | Iversen et al. |
| 6,794,499 B2 | 9/2004 | Wengel et al. |
| 6,828,105 B2 | 12/2004 | Stein et al. |
| 6,841,542 B2 | 1/2005 | Bartelmez |
| 6,965,025 B2 | 11/2005 | Gaarde et al. |
| 6,969,400 B2 | 11/2005 | Rhee et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,049,431 B2 | 5/2006 | Iversen et al. |
| 7,053,207 B2 | 5/2006 | Wengel |
| 7,060,809 B2 | 6/2006 | Wengel et al. |
| 7,084,125 B2 | 8/2006 | Wengel |
| 7,094,765 B1 | 8/2006 | Iversen et al. |
| 7,125,994 B2 | 10/2006 | Kim et al. |
| 7,145,006 B2 | 12/2006 | Kim et al. |
| 7,148,204 B2 | 12/2006 | Bennnett et al. |
| 7,179,896 B2 | 2/2007 | Kim et al. |
| 7,211,668 B2 | 5/2007 | Kim et al. |
| 7,468,418 B2 | 12/2008 | Iversen et al. |
| 7,534,879 B2 | 5/2009 | van Deutekom |
| 7,569,575 B2 | 8/2009 | Sorensen et al. |
| 7,572,582 B2 | 8/2009 | Wengel et al. |
| 7,618,814 B2 | 11/2009 | Bentwich |
| 7,807,159 B2 | 10/2010 | Chin et al. |
| 7,807,816 B2 | 10/2010 | Wilton et al. |
| 7,838,657 B2 | 11/2010 | Singh et al. |
| 7,887,793 B2 | 2/2011 | Tremblay |
| 7,888,012 B2 | 2/2011 | Iversen et al. |
| 7,935,816 B2 | 5/2011 | Li |
| 7,943,762 B2 | 5/2011 | Weller et al. |
| 7,977,472 B2 | 7/2011 | Beigelman et al. |
| 8,066,996 B2 | 11/2011 | Calleja et al. |
| 8,076,476 B2 | 12/2011 | Reeves et al. |
| 8,779,128 B2 | 7/2014 | Hanson et al. |
| 8,785,410 B2 | 7/2014 | Iversen et al. |
| 9,322,019 B2 | 4/2016 | Dickson |
| 10,006,031 B2 | 6/2018 | Iversen et al. |
| 10,106,795 B2 | 10/2018 | Dickson et al. |
| 2003/0074680 A1 | 4/2003 | Lee et al. |
| 2003/0123191 A1 | 7/2003 | Kasamatsu et al. |
| 2003/0129171 A1 | 7/2003 | Grobet et al. |
| 2003/0235845 A1 | 12/2003 | Ommen et al. |
| 2004/0242528 A1 | 12/2004 | Hagstrom et al. |
| 2004/0265879 A1 | 12/2004 | Iversen et al. |
| 2004/0266720 A1 | 12/2004 | Iversen et al. |
| 2005/0124566 A1 | 6/2005 | Robin et al. |
| 2006/0030522 A1 | 2/2006 | Knopf et al. |
| 2006/0276425 A1 | 12/2006 | Mourich et al. |
| 2006/0287268 A1 | 12/2006 | Iversen et al. |
| 2007/0105807 A1 | 5/2007 | Sazani et al. |
| 2007/0122821 A1 | 5/2007 | Iversen et al. |
| 2007/0249538 A1 | 5/2007 | Sazani et al. |
| 2009/0005308 A1 | 1/2009 | Knopf et al. |
| 2009/0082547 A1 | 3/2009 | Iversen et al. |
| 2009/0088562 A1 | 4/2009 | Weller et al. |
| 2009/0099066 A1 | 4/2009 | Moulton et al. |
| 2009/0105139 A1 | 4/2009 | Kole et al. |
| 2009/0110689 A1 | 4/2009 | Mourich et al. |
| 2009/0246221 A1 | 10/2009 | Mourich et al. |
| 2009/0264353 A1 | 10/2009 | Orum et al. |
| 2009/0269755 A1 | 10/2009 | Aartsma-Rus et al. |
| 2009/0312532 A1 | 12/2009 | Deutekom et al. |
| 2010/0003218 A1 | 1/2010 | Duan et al. |
| 2010/0016215 A1 | 1/2010 | Moulton et al. |
| 2010/0130591 A1 | 5/2010 | Sazani et al. |
| 2010/0184670 A1 | 7/2010 | Mourich et al. |
| 2010/0272734 A1 | 10/2010 | Berger et al. |
| 2011/0269820 A1 | 11/2011 | Singh et al. |
| 2011/0294753 A1 | 12/2011 | De Kimpe et al. |
| 2011/0312086 A1 | 12/2011 | Deutekom |
| 2012/0059042 A1 | 3/2012 | Platenburg et al. |
| 2012/0202752 A1 | 8/2012 | Lu |
| 2013/0085139 A1 | 4/2013 | Dickson et al. |
| 2013/0211062 A1 | 8/2013 | Watanabe et al. |
| 2014/0045916 A1 | 2/2014 | Iversen et al. |
| 2014/0057964 A1 | 2/2014 | Popplewell et al. |
| 2014/0113955 A1 | 4/2014 | De Kimpe et al. |
| 2014/0315862 A1 | 10/2014 | Kaye |
| 2014/0323544 A1 | 10/2014 | Bestwick et al. |
| 2014/0323956 A1 | 10/2014 | Mendell et al. |
| 2014/0343266 A1 | 11/2014 | Watanabe et al. |
| 2015/0045413 A1 | 2/2015 | De Visser et al. |
| 2015/0073140 A1 | 3/2015 | Hanson et al. |
| 2015/0166996 A1 | 6/2015 | Deutekom |
| 2015/0203849 A1 | 7/2015 | Deutekom |
| 2016/0281092 A1 | 9/2016 | Iversen et al. |
| 2017/0022502 A1 | 1/2017 | Dickson et al. |
| 2018/0327749 A1 | 11/2018 | Iversen |
| 2018/0355358 A1 | 12/2018 | Schnell |
| 2019/0048350 A1 | 2/2019 | Dickson |

FOREIGN PATENT DOCUMENTS

| | | |
|---|---|---|
| EP | 2125006 | 10/2013 |
| EP | 3359668 | 8/2018 |
| JP | 2018-518148 | 7/2018 |
| JP | 2018-530560 | 10/2018 |
| WO | WO1993001286 | 1/1993 |
| WO | WO1993024510 | 12/1993 |
| WO | WO1994004678 | 3/1994 |
| WO | WO199426887 | 11/1994 |
| WO | WO1994025591 | 11/1994 |
| WO | WO1994026764 | 11/1994 |
| WO | WO19973461 | 9/1997 |
| WO | WO199740854 | 11/1997 |
| WO | WO199902667 | 1/1999 |
| WO | WO200020432 | 4/2000 |
| WO | WO200172765 | 10/2001 |
| WO | WO200183740 | 11/2001 |
| WO | WO2004043977 | 5/2004 |
| WO | WO2004097017 | 11/2004 |
| WO | WO2005107447 | 11/2005 |
| WO | WO2006000057 | 1/2006 |
| WO | WO2006083183 | 8/2006 |
| WO | WO2006086667 | 8/2006 |
| WO | WO2006116269 | 11/2006 |
| WO | WO2007002390 | 1/2007 |

(56) References Cited

FOREIGN PATENT DOCUMENTS

| WO | WO2007058894 | 5/2007 |
|---|---|---|
| WO | WO2008005019 | 1/2008 |
| WO | WO2008036127 | 3/2008 |
| WO | WO2008051306 | 5/2008 |
| WO | WO2008097541 | 8/2008 |
| WO | WO2008131807 | 11/2008 |
| WO | WO2008153933 | 12/2008 |
| WO | WO2009005793 | 1/2009 |
| WO | WO2009008725 | 1/2009 |
| WO | WO2009064471 | 5/2009 |
| WO | WO2009086469 | 7/2009 |
| WO | WO2009088895 | 7/2009 |
| WO | WO2010019261 | 2/2010 |
| WO | WO2010048586 | 4/2010 |
| WO | WO2010080554 | 7/2010 |
| WO | WO2010115993 | 10/2010 |
| WO | WO2010120820 | 10/2010 |
| WO | WO2010129406 | 11/2010 |
| WO | WO2010148249 | 12/2010 |
| WO | WO2011057350 | 5/2011 |
| WO | WO2011150408 | 12/2011 |
| WO | WO2012043730 | 4/2012 |
| WO | WO2012150960 | 11/2012 |
| WO | WO2013053928 | 4/2013 |
| WO | WO2013074834 | 5/2013 |
| WO | WO2013112053 | 8/2013 |
| WO | WO2014100714 | 6/2014 |
| WO | WO2014153220 | 9/2014 |
| WO | WO2014172448 | 10/2014 |
| WO | WO2015035231 | 3/2015 |
| WO | WO2016149659 | 9/2016 |
| WO | WO2017062835 | 4/2017 |

OTHER PUBLICATIONS

USPTO; Notice of Allowance dated Sep. 29, 2010 in U.S. Appl. No. 11/433,724.
USPTO; Restriction Requirement dated Jun. 19, 2012 in U.S. Appl. No. 12/983,798.
USPTO; Non-Final Office Action dated Sep. 6, 2013 in U.S. Appl. No. 12/983,798.
USPTO; Non-Final Office Action dated Jan. 24, 2013 in U.S. Appl. No. 12/983,798.
USPTO; Notice of Allowance dated Mar. 13, 2014 in U.S. Appl. No. 12/983,798.
USPTO; Restriction Requirement dated Jun. 13, 2013 in U.S. Appl. No. 13/644,363.
USPTO; Non-Final Office Action dated Jul. 24, 2013 in U.S. Appl. No. 13/644,363.
USPTO; Non-Final Office Action dated Jan. 16, 2014 in U.S. Appl. No. 13/644,363.
USPTO; Non-Final Office Action dated Jun. 2, 2014 in U.S. Appl. No. 13/644,363.
USPTO; Restriction Requirement dated Aug. 5, 2015 in U.S. Appl. No. 14/323,349.
USPTO; Non-Final Office Action dated Dec. 10, 2015 in U.S. Appl. No. 14/323,349.
USPTO; Restriction Requirement dated Jan. 14, 2015 in U.S. Appl. No. 14/504,453.
USPTO; Non-Final Office Action dated May 27, 2015 in U.S. Appl. No. 14/504,453.
USPTO; Notice of Allowance dated Sep. 10, 2015 in U.S. Appl. No. 14/504,453.
USPTO; Notice of Allowance dated Dec. 29, 2015 in U.S. Appl. No. 14/504,453.
USPTO; Requirement for Restriction dated Nov. 17, 2016 in U.S. Appl. No. 15/078,029.
USPTO; Non-Final Office Action dated Jun. 15, 2017 in U.S. Appl. No. 15/078,029.
USPTO; Non-Final Office Action dated Aug. 1, 2017 in U.S. Appl. No. 15/177,244.
USPTO; Final Office Action dated Feb. 8, 2018 in U.S. Appl. No. 15/078,029.
USPTO; Notice of Allowance dated Feb. 20, 2018 in U.S. Appl. No. 15/177,244.
USPTO; Notice of Allowance dated Jun. 13, 2018 in U.S. Appl. No. 15/078,029.
USPTO; Non-Final Office Action dated Dec. 14, 2018 in U.S. Appl. No. 16/129,680.
USPTO; Requirement for Restriction dated Jan. 7, 2019 in U.S. Appl. No. 15/559,257.
USPTO; Non-Final Office Action dated Apr. 9, 2019 in U.S. Appl. No. 15/559,257.
USPTO; Requirement for Restriction dated May 3, 2019 in U.S. Appl. No. 15/765,466.
USPTO; Notice of Allowance dated May 13, 2019 in U.S. Appl. No. 16/129,680.
International Search Report for Application No. PCT/AU2005/000943 dated Oct. 20, 2005.
International Search Report for Application No. PCT/EP2007/061211 dated Dec. 18, 2008.
International Search Report for Application No. PCT/US1994/005181 dated Oct. 7, 1994.
International Search Report for Application No. PCT/US1999/022448 dated Dec. 23, 1999.
International Search Report for Application No. PCT/US2000/008174 dated Jul. 25, 2000.
International Search Report for Application No. PCT/US2001/014410 dated Mar. 6, 2002.
International Search Report for Application No. PCT/US2006/004797 dated Feb. 22, 2007.
International Preliminary Report on Patentability for Application No. PCT/US2006/004797 dated Feb. 9, 2006.
International Search Report for Application No. PCT/US2006/043651 dated Jun. 27, 2007.
International Search Report for Application No. PCT/US2007/010556 dated Mar. 13, 2008.
International Search Report for Application No. PCT/US2008/088339 dated Jun. 4, 2009.
International Search Report for Application No. PCT/US2009/061960 dated Apr. 6, 2010.
International Search Report for Application No. PCT/US2009/068599 dated May 21, 2010.
International Search Report & Written Opinion for Application No. PCT/US2016/023239 dated Sep. 9, 2016.
International Search Report for Application No. PCT/US2016/056093 dated Apr. 28, 2017.
Written Opinion of the International Searching Authority for Application No. PCT/US2016/056093 dated Apr. 28, 2017.
Invitation to Pay Additional Fees and where Applicable, Protest Fee for Application No. PCT/US2016/23239 dated Jun. 22, 2016.
Written Opinion of the International Searching Authority for Application No. PCT/US2009/068599 dated May 21, 2010.
Written Opinion of the International Searching Authority for Application No. PCT/US2009/061960 dated Apr. 6, 2010.
Written Opinion of the International Searching Authority for Application No. PCT/US2008/088339 dated Jun. 4, 2009.
Written Opinion of the International Searching Authority for Application No. PCT/US2007/010556 dated Mar. 13, 2008.
Written Opinion of the International Searching Authority for Application No. PCT/US2006/043651 dated Jun. 27, 2007.
Written Opinion of the International Searching Authority for Application No. PCT/EP2007/0061211 dated Dec. 18, 2008.
Written Opinion of the International Searching Authority for Application No. PCT/AU2005/000943 dated Oct. 20, 2005.
Written Opinion of the International Searching Authority for Application No. PCT/US2006/004797 dated Oct. 31, 2006.
CIPO; Office Action dated Apr. 5, 2016 in Canadian Application No. 2,596,506.
EP; Office Action dated Sep. 24, 2010 in EP Application No. 2006734779.
AU; Office Action dated Jun. 7, 2011 in AU Application No. 2006213686.

(56) References Cited

OTHER PUBLICATIONS

EP; Office Action dated Sep. 25, 2013 in EP Application No. 2006734779.
AU; Office Action dated Jan. 17, 2014 in AU Application No. 2003201250.
EP; Office Action dated Aug. 14, 2014 in EP Application No. 2006734779.
AU; Notice of Allowance dated Apr. 20, 2015 in AU Application No. 2003201250.
AU; Office Action dated Oct. 7, 2016 in AU Application No. 2015203791.
AU; Office Action dated Jan. 6, 2017 in AU Application No. 2015203791.
AU; Notice of Acceptance for Patent Application dated Jun. 15, 2017 in AU Application No. 2015203791.
CA; Office Action dated Mar. 5, 2018 in CA Application No. 2596506.
CA; Notice of Allowance dated Apr. 4, 2019 in CA Application No. 2596506.
EPO; Extended Search Report dated Nov. 20, 2018 in EP Application No. 16765858.2.
EPO; Extended Search Report dated May 3, 2019 in EP Application No. 16854468.2.
IL; Office Action dated Jul. 8, 2019 in the IL Application No. 258069.
Aartsma-Rus et al., "Antisense-Mediated Exon Skipping: A Versatile Tool with Therapeutic and Research Applications," RNA, vol. 13, pp. 1609-1624, (2007).
Aartsma-Rus et al., "Theoretic Applicability of Antisense-Mediated Exon Skipping for Duchenne Muscular Dystrophy Mutations," Human Mutation, vol. 30(3), pp. 293-299, (2009).
Aartsma-Rus et al., "Antisense-Mediated Exon Skipping for Duchenne Muscular Dystrophy," Human Gene Therapy, vol. 20, pp. 660-661, (2009).
Aartsma-Rus et al., "Theoretic Applicability of Anitsense Mediated Exon Skipping for Duchenne Muscular Dystrophy Mutations," Human Mutation, vol. 30(3), pp. 293-299; p. 294, table 1, (2009).
Abbs et al., "Best Practice Guidelines on Molecular Diagnostics in Duchenne/Becker Muscular Dystrophies," Neuromuscular Disorders, vol. 20(6), pp. 422-427, (2010).
Agrawal et al., "Site-Specific Excision from RNA by Rnase H and Mixed-Phosphate-Backbone Oligodeoxynucleotides," Proceedings of the National Academy of Sciences of USA, vol. 87(4), pp. 1401-1405, (1990).
Agrawal, "Importance of Nucleotide Sequence and Chemical Modifications of Antisense Oligonucleotides," Biochim Biophys Acta, vol. 1489, pp. 53-68, (1999).
Alter et al., "Systemic Delivery of Morpholino Oligonucleotide Restores Dystrophin Expression Bodywide and Improves Dystrophic Pathology," Nat Med, vol. 12, pp. 175-177, (2006).
Altschul et al., "Gapped BLAST and PSI-BLAST: A New Generation of Protein Database Search Programs," Nucleic Acids Research, vol. 25(17), pp. 3389-3402, (1997).
Amali et al., "Up-Regulation of Muscle-Specific Transcription Factors During Embryonic Somitogenesis of Zebrafish (*Danio rerio*) by Knock-Down of Myostatin-1," Developmental Dynamics, vol. 229, pp. 847-856, 2004.
Amantana et al., "Pharmacokinetics and Biodistribution of Phosphorodiamidate Morpholino Antisense Oligomers," Curr Opin Pharmacol, vol. 5, pp. 550-555, (2005).
Arora et al., "Neutrally Charged Phosphorodiamidate Morpholino Antisense Oligomers: Uptake, Efficacy and Pharmacokinetics," Current Pharmaceutical Biotechnology, vol. 5, pp. 431-439, (2004).
Bailey et al., "Cationic Oligonucleotides can Mediate Specific Inhibition of Gene Expression in Xenopus Oocytes," Nucleic Acids Research, vol. 26(21), pp. 4860-4867, (1998).
Barawkar et al., "Synthesis, Biophysical Properties, and Nuclease Resistance Properties of Mixed Backbone Oligodeoxynucleotides Containing Cationic Internucleoside Guanidinium Linkages: Deoxynucleic Guanidine/ DNA Chimeras," Proceedings of the National Academy of Sciences of the USA, vol. 95(19), pp. 11047-11052, (1998).
Benner et al., "Synthetic Biology," Nature Reviews Genetics, vol. 6(7), pp. 553-543, (2005).
Bennett et al., "Antisense Therapy for Angioplasty Restenosis," Circulation, vol. 92(7), pp. 1981-1993, (1995).
Berridge et al., "Characterization of the Cellular Reduction of 3-(4,5-Dimethylthiazol-2-yl)-2,5-Diphenyltetrazolium Bromide (MTT): Subcellular Localization, Substrate Dependence, and Involvement of Mitochondrial Electron Transport in Mtt Reduction," Arch Biochem Biophys, vol. 303, pp. 747-482, (1993).
Bestas Burcu et al., "Design and Application of Biospecific Splice-Switching Oligonucleotides," Nucleic Acid Therapeutics, vol. 24(1), (Feb. 2014).
Blommers et al., "An Approach to the Structure Determination of Nucleic Acid Analogues Hybridized to RNA. NMR Studies of a Duplex Between 2'-0Me RNA and an Oligonucleotide Containing a Single Amide Backbone Modification," Nucleic Acids Research, vol. 22(20), pp. 4187-4194, (1994).
Bogdanovich et al., "Functional Improvement of Dystrophic Muscle by Myostatin Blockade," Nature, vol. 420, pp. 418-421, (2002). Abstract only.
Bogdanovich et al., "Myostatin Propeptide-Mediated Amelioration of Dystrophic Pathophysiology,"FASEB J, vol. 19, pp. 543-549, (2005).
Bonham et al., "An Assesment of the Antisense Properties of Rnase H-Competent and Steric-Blocking Oligomers," Nucleic Acids Research, vol. 23(7), pp. 1197-1203, (1995). Abstract only.
Boudvillain et al., "Transplation-Modified Oligo (2'-O-Methyl Ribonucleotide)s: A New Tool for Selective Modulation of Gene Expression," Biochemistry, vol. 36(10), pp. 2925-2931, (1997). Abstract only.
Bowles et al., "Phase 1 Gene Therapy for Duchenne Muscular Dystrophy Using a Translational Optimized AAV Vector," Molecular Therapy, vol. 20(2), pp. 443-455, (2012).
Branch et al., "A Good Antisense Molecule is Hard to Find," Trends in Biochemistry Sciences, vol. 23(2): pp. 45-50, (1998).
Brown et al., "Dystrophic Phenotype Induced In Vitro by Antibody Blockade of Muscle Alpha-Dystroglycan-Laminin Interaction," Journal of Cell Science, vol. 112(2), pp. 209-216, (1999).
Fairbrother et al., "RESCUE-ESE Identifies Candidate Exonic Splicing Enhancers in Vertebrate Exons," Nucleic Acids Research, vol. 32, pp. W187-W190, (2004).
Carnac et al., "Myostatin: Biology and Clinical Relevance," Mini Rev Med Chem, vol. 6, pp. 765-770, (2006).
Cartegni et al., "Listening to Silence and Understanding Nonsense: Exonic Mutations that Affect Splicing," Nat Rev Genet, vol. 3, pp. 285-298, (2002).
Cartegni et al., "ESEfinder: A Web Resource to Identify Exonic Splicing Enhancers," Nucleic Acids Res, vol. 31, pp. 3568-3571, (2003).
Chirila et al., "The Use of Synthetic Polymers for Delivery of Therapeutic Antisense Oligodeoxynucleotides," Biomaterials, vol. 23, pp. 321-342, (2002). Abstract only.
Chiu et al., "siRNA Function in RNAi: A Chemical Modification Analysis," RNA, vol. 9, pp. 1034-1048, (2003).
Collins & Morgan, "Duchenne's Muscular Dystrophy: Animal Models used to Investigate Pathogenesis and Develop Therapeutic Strategies," International Journal of Experimental Pathology, vol. 84(4), pp. 165-172, (2003).
Cory et al., "Use of an Aqueous Soluble Tetrazolium/Formazan Assay for Cell Growth Assays in Culture," Cancer Communications, vol. 3(7), pp. 207-212, (1991).
Cross et al., "Solution Structure of an RNA × DNA Hybrid Duplex Containing a 3'-Thioformacetal Linker and an RNA A-Tract," Biochemistry, vol. 36(14), pp. 4096-4107, (1997). Abstract only.
Dagle et al., "Targeted Elimination of Zygotic Messages in Xenopus Laevis Embryos by Modified Oligonucleotides Possessing Terminal Cationic Linkages," Nucleic Acids Research, vol. 28(10), pp. 2153-2157, (2000).

(56) References Cited

OTHER PUBLICATIONS

Dennler et al., "Direct Binding of Smad3 and Smad4 to Critical TGF Beta-Inducible Elements in the Promoter of Human Plasminogen Activator Inhibitor—Type 1 Gene," EMBO J, vol. 17, pp. 3091-3100, (1998).
Deveraux et al., "A Comprehensive Set of Sequence Analysis Programs for the VAX," Nucleic Acids Research, vol. 12, pp. 387-395, (1984).
Ding, D. et al., "An Oligodeoxyribonucleotide N34 P54 Phosphoramidate Duplex Forms an A-Type Helix in Solution," Nucleic Acids Research, vol. 24(2), pp. 354-360, (1996).
Dokka et al., "Novel Non-Endocytic Delivery of Antisense Oligonucleotides," Advanced Drug Delivery Reviews, vol. 44(1), pp. 35-49, (2000).
Dominski et al., "Restoration of Correct Splicing in Thalassemic PremRNA by Antisense Oligonucleotides," Proceedings of the National Academy of Sciences USA, vol. 90, pp. 8673-8677, (1993).
Dumonceaux et al., "Combination of Myostatin Pathway Interference and Dystrophin Rescue Enhances Tetanic and Specific Force in Dystrophic MDX Mice," Molecular Therapy, vol. 18, pp. 881-887, (2010).
Dunckley et al., "Modification of Splicing in the Dystrophin Gene in Cultured Mdx Muscle Cells by Antisense Oligoribonucleotides," Human Molecular Genetics, vol. 7, pp. 1083-1090, (1998).
Egholm et al., "PNA Hybridizes to Complementary Oligonucleotides Obeying the Watson-Crick Hydrogen-Bonding Rules," Nature, vol. 365(6446), pp. 566-568, (1993). Abstract only.
EMBL Accession No. DQ927047, *Homo sapiens* Isolate AFRAM_A02 Myostatin (GDF8), pp. 1-2; downloaded from the internet, Apr. 4, 2017, (Dec. 15, 2006).
Fairbrother et al., "Predictive Identification of Exonic Splicing Enhancers in Human Genes," Science, vol. 297, pp. 1007-1013, (2002).
Fakhfakh et al., "Blocking the Myostatin Signal with a Dominant Negative Receptor Improves the Success of Human Myoblast Transplantation in Dystrophic Mice," Molecular Therapy, vol. 19, pp. 204-210, (2011).
Felgner et al., "Lipofection: A Highly Efficient, Lipid-Mediated DNA-Transfection Procedure," PNAS, vol. 84(21), pp. 7413-7417, (1987).
Foster, "Eye Evolution: Two Eyes can be Better than One," Current Biology, vol. 19, pp. R208-R210, (2009).
Foster et al., "Adeno-Associated Virus-8-Mediated Intravenous Transfer of Myostatin Propeptide Leads to Systemic Functional Improvements of Slow but Not Fast Muscle," Rejuvenation Research, vol. 12, pp. 85-94, (2009).
Friedman et al., "Correction of Aberrant Splicing of the Cystic Fibrosis Transmembrane Conductance Regulator (CFTR) Gene by Antisense Oligonucleotides," Journal of Biological Chemistry, vol. 274, pp. 36193-36199, (1999).
Gait et al., "Synthetic Analogues of Polynucleotides XII. Synthesis of Thymidine Derivatives Containing an Oxyacetamido- or an Oxyformamido-Linkage Instead of a Phosphodiester Group," Journal of the Chemical Society, vol. 14, pp. 1684-1686, (1974).
Gebski et al., "Terminal Antisense Oligonucleotide Modifications can Enhance Induced Exon Skipping," Neuromuscular Disorders, vol. 15, pp. 622-629, (2005).
Gebski et al., "Morpholino Antisense Oligonucleotide Induced Dystrophin Exon 23 Skipping in Mdx Mouse Muscle," Human Molecular Genetics, vol. 12, pp. 1801-1811, (2003).
Gee et al., "Assessment of High-Affinity Hybridization, RNase H Cleavage and Covalent Linkage in Translation Arrest by Antisense Oligonucleotides," Antisense Nucleic Acid Drug Development, vol. 8(2), pp. 103-111, (1998). Abstract only.
Ghahramani et al., "RNAi-Mediated Knockdown of Dystrophin Expression in Adult Mice does not Lead to Overt Muscular Dystrophy Pathology," Hum Mol Genet, vol. 17, pp. 2622-2632, (2008).

Gonzalez-Cadavid et al., "Organization of the Human Myostatin Gene and Expression in Healthy Men and HIV-Infected Men with Muscle Wasting," PNAS, vol. 95(25), pp. 14938-14943, (1998).
Graham et al., "Towards a Therapeutic Inhibition of Dystrophin Exon 23 Splicing in Mdx Mouse Muscle Induced by Antisense Oligoribonucleotides (Splicomers): Target Sequence Optimisation using Oligonucleotide Arrays," Journal of Gene Medicine, vol. 6, pp. 1149-1158, (2004).
Grobet et al., "A Deletion in the Bovine Myostatin Gene Causes the Double-Muscled Phenotype in Cattle," Nature Genetics, vol. 17, pp. 71-74, (1997).
Haidet et al., "Long-Term Enhancement of Skeletal Muscle Mass and Strength by Single Gene Administration of Myostatin Inhibitors," Proceedings of the National Academy of Sciences USA, vol. 105, pp. 4318-4322, (2008).
Hausen et al., "Ribonuclease H. An Enzyme Degrading the RNA Moiety of DNA-RNA Hybrids," European Journal of Biochemistry, vol. 14, pp. 278-283, (1970).
Hirao, "Unnatural Base Pair Systems for DNA/RNA-Based Biotechnology," Current Opinion in Chemical Biology, vol. 10(6), pp. 622-627, (2006).
Hudson et al., "High Avidity scFv Multimers; Diabodies and Triabodies," Journal of Immunological Methods, vol. 231(1), pp. 177-189, (1999).
Hudziak et al. "Antiproliferative Effects of Steric Blocking Phosphorodiamidate Morpholino Antisense Agents Directed Against C-MYC," Antisense & Nucleic Acid Drug Development, vol. 10(3), pp. 163-176, (2000). Abstract only.
Hudziak et al., "Resistance of Morpholino Phosphorodiamidate Oligomers to Enzymatic Degradation," Antisense & Nucleic Acid Drug Development, vol. 6, pp. 267-272, (1996). Abstract only.
Iversen, "Phosphorodiamidate Morpholino Oligomers: Favorable Properties for Sequence-Specific Gene Inactivation," Current Opinion in Molecular Therapeutics, vol. 3(3), pp. 235-238, (2001).
Iyer et al., "The Automated Synthesis of Sulfur-Containing Oligodeoxyribonucleotides Using 3H-1,2-Benzodithiol-3-One 1,1-Dioxide as a Sulfur-Transfer Reagent," Journal of Organic Chemistry, vol. 55, pp. 4693-4699, (1990).
Jagjeet K. Kang et al., "Antisense-Induced Myostatin Exon Skipping Leads to Muscle Hypertrophy in Mice Following Octa-Guanidine Morpholino Oligomer Treatment," Molecular Therapy, vol. 19(1), pp. 159-164, (Jan. 2011).
Jearawiriyapaisarn et al., "Long-Term Improvement in Mdx Cardiomyopathy After Therapy with Peptide-Conjugated Morpholino Oligomers," Cardiovascular Research, vol. 85, pp. 444-453, (2010).
Jen et al., "Suppression of Gene Expression by Targeted Disruption of Messenger RNA: Available Options and Current Strategies," Stem Cells, vol. 18, pp. 307-319, (2000).
Joulia et al., "Mechanisms Involved in the Inhibition of Myoblast Proliferation and Differentiation by Myostatin," Experimental Cell Research, vol. 286, pp. 263-275, (2003). Abstract only.
Kang et al., "Antisense-Induced Myostatin Exon Skipping Leads to Muscle Hypertrophy in Mice Following Octa-guanidine Morpholino Oligomer Treatment," Molecular Therapy, vol. 19(1), pp. 159-164, (2011).
Kernaladewi et al., "Dual Exon Skipping in Myostatin and Dystrophin for Duchenne Muscular Dystrophy," BMC Medical Genomics, vol. 4, p. 36-45, (2011).
Kinali et al., "Local Restoration of Dystrophin Expression with the Morpholino Oligomer AVI-4658 in Duchenne Muscular Dystrophy: A Single-Blind, Placebo-Controlled, Dose-Escalation, Proof-of-Concept Study," Lancet Neurol, vol. 8, pp. 918-928, (2009).
Kirk et al., "Myostatin Regulation During Skeletal Muscle Regeneration," Journal of Cell Physiology, vol. 184(3), pp. 356-363, (2000). Abstract only.
Kool, "Replacing the Nucleobases in DNA with Designer Molecules," Accounts of Chemical Research, vol. 35(11), pp. 936-943, (2002).
Koppanati et al., "Improvement of the MDX Mouse Dystrophic Phenotype by Systemic in Utero AAV8 Delivery of a Minidystrophin Gene," Gene Therapy, vol. 17(11), pp. 1355-1362, (2010).

(56) References Cited

OTHER PUBLICATIONS

Krainer et al., "Disruption if an SF2/ASF-Dependent Exonic Splicing Enhancer in SMN2 Causes Spinal Muscular Atrophy in the Absence of SMN1," Nature Genetics, vol. 30, pp. 377-384, (2002).
Kruegar et al., "Synthesis and Properties of Size-Expanded DNAs: Toward Designed, Functional Genetic Systems," Accounts of Chemical Research, vol. 40(2), pp. 141-150, (2007).
Langley et al., "Myostatin Inhibits Myoblast Differentiation by Down-Regulating MyoD Expression," J Biol Chem, vol. 277, pp. 49831-49840, (2002).
Lappalainen et al., "Cationic Liposomes Improve Stability and Intracellular Delivery of Antisense Oligonucleotides into CaSki Cells," Biochim Biophys ACTA, vol. 1196(2), pp. 201-208, (1994). Abstract only.
Lappalainen et al., "Cationic Liposomes Mediated Delivery of Antisense Oligonucleotides Targeted to HPV 16 E7 mRNA in CaSki Cells," Antiviral Research, vol. 23, p. 119-130, (1994).
Lesnikowski et al., "Octa(Thymidine Methanephosphonates) of Partially Defined Sterochemistry: Synthesis and Effect of Chirality at Phosphorus on Binding to Pentadecadecadeoxyriboadenylic Acid," Nucleic Acids Research, vol. 18(8), pp. 2109-2115, (1990).
Levin et al., "Position-Dependent Effects of Locked Nucleic Acid (LNA) on DNA Sequencing and PCR Primers," Nucleic Acids Research, vol. 34, e 142, pp. 1-11, (2006).
Limbach et al., "Summary: The Modified Nucleosides of RNA ," Nucleic Acids Research, vol. 22(12), pp. 2183-2196, (1994).
Linkletter et al., "Solid-Phase Synthesis of Positively Charged Deoxynucleic Guanidine (DNG) Modified Oligonucleotides Containing Neutral Urea Linkages: Effect of Charge Deletions on Binding and Fidelity," Bioorganic & Medicinal Chemistry, vol. 8(11), pp. 1893-1901, (2000). Abstract only.
Lou et al., "Synthetic Hydrogels as Carriers in Antisense Therapy: Preliminary Evaluation of an Oligodeoxynucleotide Covalent Conjugate with a Copolymer of 1-Vinyl-2-Pyrrolidinone and 2-Hydroxyethyl Methacrylate," Journal of Biomaterials Applications, vol. 15(4), pp. 307-320, (2001). Abstract only.
Lu-Nguyen et al., "Combination Antisense Treatment for Destructive Exon Skipping of Myostatin and Open Reading Frame Rescue of Dystrophin in Neonatal mdx Mice," Molecular Therapy, vol. 23(8), pp. 1341-1348, (Aug. 2015).
Lu-Nguyen, "Mouse Open-Field Behavioral Activity," Supplementary Materials and Methods, 2 Pages.
Malerba et al., "Dual Myostatin and Dystrophin Exon Skipping by Morpholino Nucleic Acid Oligomers Conjugated to a Cell-Penetrating Peptide is a Promising Therapeutic Strategy for the Treatment of Duchenne Muscular Dystrophy," Molecular Therapy—Nucleic Acids, vol. 1, p. e62, (Dec. 2012).
Martin et al., "Ein Neuer Zugang Zu 2'-O-Alkylribonucleosiden Und Eigenschaften Deren Oligonucleotide," Helvetica Chimica Acta, vol. 78, pp. 486-504, (1995).
Martin et al., "Overexpression of Galgt2 in Skeletal Muscle Prevents Injury Resulting from Eccentric Contractions in Both MDX and Wild-Type Mice," American Journal of Physiology—Cell Physiology, vol. 296, pp. 476-488, (2009).
McDonald et al., "The 6-Minute Walk Test as a New Outcome Measure in Duchenne Muscular Dystrophy," Muscle & Nerve, vol. 41(4), pp. 500-510, (2010).
McDonald et al., "The 6-Minute Walk Test in Duchenne/Becker Muscular Dystrophy: Longitudinal Observations," Muscle & Nerve, vol. 42(6), pp. 966-974, (2010).
McGreevy et al., "Animal Models of Duchenne Muscular Dystrophy: From Basic Mechanisms to Gene Therapy," Disease Models & Mechanisms, vol. 8(3), pp. 195-213, (2015).
McPherron et al., "Regulation of Skeletal Muscle Mass in Mice by a New TGF-Beta Superfamily Member," Nature, vol. 387(6628), pp. 83-90, (1997). Abstract only.
McPherron et al., "Double Muscling in Cattle Due to Mutations in the Myostatin Gene," PNAS, vol. 94(23), pp. 12457-12461, (1997).
Mertes et al., "Synthesis of Carbonate Analogs of Dinucleosides. 3-Thymidinyl 5-Thymidinyl Carbonate, 3-Thymidinyl 5-(5-Fluoro-2-Deoxyuridinyl) Carbonate, and 3-(5-Fluoro-2-Deoxyuridinyl) 5-Thymidinyl Carbonate," Journal of Medicinal Chemistry, vol. 12(1), pp. 154-157, (1969).
Micklefield, J., "Backbone Modification of Nucleic Acids: Synthesis, Structure and Therapeutic Applications," Current Medicinal Chemistry, vol. 8(10), pp. 1157-1179, (2001). Abstract only.
Miyada et al., "Oligomer Hybridization Techniques," Methods in Enzymology, vol. 154, pp. 94-107, (1987).
Morcos et al., "Vivo-Morpholinos: A Non-Peptide Transporter Delivers Morpholinos into a Wide Array of Mouse Tissues," Biotechniques, vol. 45 pp. 613-614, 616, 618 passim, (2008).
Moulton et al., "Peptide-Assisted Delivery of Steric-Blocking Antisense Oligomers," Current Opinion in Molecular Therapeutics, vol. 5(2), pp. 123-132, (2003). Abstract only.
Moulton et al., "HIV Tat Peptide Enhances Cellular Delivery of Antisense Morpholino Oligomers," Antisense Nucleic Acid Drug Development, vol. 13(1), pp. 31-43, (2003). Abstract only.
Moulton et al., "Cellular Uptake of Antisense Morpholino Oligomers Conjugated to Arginine-Rich Peptides," Bioconjugate Chemistry, vol. 15(2), pp. 290-299, (2004). Abstract only.
Mourich et al., "Antisense Targeting of cFLIP Sensitizes Activated T Cells to Undergo Apoptosis and Desensitizes Responses to Contact Dermatitis," Journal of Investigative Dermatology, vol. 129(8), pp. 1945-1953, (2009).
Muyldermans et al., "Recognition of Antigens by Single-Domain Antibody Fragments: The Superfluous Luxury of Paired Domains," Trends in Biochemical Sciences, vol. 26(4), pp. 230-235, (2001).
Nielsen et al., "Sequence-selective recognition of DNA by strand displacement with a thymine-substituted polyamide," Science, vol. 254(5037), pp. 1497-1500, (1991).
Nuttall et al., "Immunoglobulin VH Domains and Beyond: Design and Selection of Single-Domain Binding and Targeting Reagents," Current Pharmaceutical Biotechnology, vol. 1(3), pp. 253-263, (2000).
Obika et al., "Synthesis of 2'-O,4'-C-Methyleneuridine and -Cytidine. Novel Bicyclic Nucleosides having a Fixed C3, -Endo Sugar Puckering," Tetrahedron Letters, vol. 38(50), p. 8735, (1997).
Obika et al., "Stability and Structural Features of the Duplexes Containing Nucleoside analogues with a fixed N-Type Conformation, 2'-O,4'-C-Mehtyleneribonueleosides," Tetrahedron Letters, vol. 39(30), p. 5401-5404, (1998).
Obika et al., "Synthesis and Properties of 3'-Amino-2',4'-BNA, A Bridged Nucleic Acid with a N3'→P5' Phosphoramidate Linkage," Bioorganic & Medicinal Chemistry, vol. 16(20), p. 9230, (2008).
Odom et al., "Gene Therapy of MDX Mice with Large Truncated Dystrophins Generated by Recombination Using rAAV6," Molecular Therapy, vol. 19(1), pp. 36-45, (2011).
Okada et al., "Current Challenges and Future Directions in Recombinant AAV-Mediated Gene Therapy of Duchenne Muscular Dystrophy," Pharmaceuticals, vol. 6(7), pp. 813-836, (2013).
Palu et al., "In Pursuit of New Developments for Gene Therapy of Human Diseases," Journal of Biotechnology, vol. 68, pp. 1-13, (1999). Abstract only.
Paola Rimessi et al., "Cationic PMMA Nanoparticles Bind and Deliver Antisense Oligoribonucleotides Allowing Restoration of Dystrophin expression in the Mdx Mouse," Molecular Therapy, vol. 17(5), pp. 820-827, (2009).
Pari et al., "Potent Antiviral Activity of an Antisense Oligonucleotide Complementary to the Intron-Exon Boundary of Human Cytomegalovirus Genes UL36 and UL37," Antimicrobiology Agents and Chemotherapy, vol. 39(5), pp. 1157-1161, (1995).
Patel et al., "The Function of Myostatin and Strategies of Myostatin Blockade—New Hope for Therapies Aimed at Promoting Growth of Skeletal Muscle," Neuromuscul Disord, vol. 15, pp. 117-126, (2005).
Poljak, "Production and Structure of Diabodies," Structure, vol. 2(12), pp. 1121-1123, (1994).
Popplewell et al., "Design of Phosphorodiamidate Morpholino Oligomers (PMOs) for the Induction of Exon Skipping of the Human DMD Gene," Mol Ther, vol. 17, pp. 554-561, (2009).

(56) References Cited

OTHER PUBLICATIONS

Popplewell et al., "Comparative Analysis of Antisense Oligonucleotide Sequences Targeting Exon 53 of the Human DMD Gene: Implications for Future Clinical Trials," Neuromuscul Disord, vol. 20, pp. 102-110, (2010).
Qiao et al., "Myostatin Propeptide Gene Delivery by Adeno-Associated Virus Serotype 8 Vectors Enhances Muscle Growth and Ameliorates Dystrophic Phenotypes in MDX Mice," Human Gene Therapy, vol. 19, pp. 241-254, (2008).
Reichmann et al., "Single Domain Antibodies: Comparison of Camel VH and Camelised Human VH Domains," Journal of Immunological Methods, vol. 231, pp. 25-38, (1999).
Revankar et al., "DNA with Altered Bases," Comprehensive Natural Products Chemistry, vol. 7(9), p. 313-339, (1999).
Rodino-Klapac et al., "Persistent Expression of FLAG-Tagged Micro-Dystrophin in Nonhuman Primates Following Intramuscular and Vascular Delivery," Molecular Therapy, vol. 18(1), pp. 109-117, (2010).
Rodino-Klapac et al., "AAV-Mediated Gene Therapy to the Isolated Limb in Rhesus Macaques," Methods in Molecular Biology, vol. 709(19), pp. 287-298, (2011).
Romesberg et al., "Beyond A, C, G and T: Augmenting Nature's Alphabet," Current Opinion in Chemical Biology, vol. 7(6), pp. 727-733, (2003).
Rondon et al., "Intracellular Antibodies (Intrabodies) for Gene Therapy of Infectious Diseases," Anuual Review of Microbiology, vol. 51, pp. 257-283, (1997).
Sazani et al., "Short-Term and Long-Term Modulation of Gene Expression by Antisense Therapeutics," Curr Opin Biotechnol, vol. 13, pp. 468-472, (2002).
Sazani et al., "Nuclear Antisense Effects of Neutral, Anionic and Cationic Oligonucleotide Analogs," Nucleic Acids Research, vol. 29, pp. 3965-3974, (2001).
Schuelke et al., "Myostatin Mutation Associated with Gross Muscle Hypertrophy in a Child," N. Eng Journal of Medicine, vol. 350, pp. 2682-2688, (2004).
Schulte et al., "Effects of Resistance Training on the Rate of Muscle Protein Synthesis in Frail Elderly People," International Journal of Sport Nutrition and Exercise Metabolism, vol. 11, pp. 111-118, (2001). Abstract only.
Shin et al., "Microdystrophin Ameliorates Muscular Dystrophy in the Canine Model of Duchenne Muscular Dystrophy," Molecular Therapy, vol. 21(4), pp. 750-757, (2013).
Sierakowska et al., "Repair of Thalassemic Human β-Globin mRNA in Mammalian Cells by Antisense Oligonucleotides," Proc Natl Acad Sci USA, vol. 93, pp. 12840-12844, (1996).
Smith et al., "An Increased Specificity Score Matrix for the Prediction of SF2/ASF-Specific Exonic Splicing Enhancers," Hum Mol Genet, vol. 15, pp. 2490-2508, (2006).
Spitali et al., "Accurate Quantification of Dystrophin mRNA and Exon Skipping Levels in Duchenne Muscular Dystrophy," Lab Invest, vol. 90, pp. 1396-1402, (2010).
Stein et al., "A Specificity Comparison of Four Antisense Types: Morpholino, 2'-O-Methyl RNA, DNA, and Phosphorothioate DNA," Antisense Nucleic Acid Drug Development, vol. 7(3), pp. 151-157, (1997). Abstract only.
Stojdl et al., "SR Protein Kinases: The Splice of Life," Biochemistry and Cell Biology—Biochimie Et Biologie Cellulaire, vol. 77, pp. 293-298, (1999).
Summerton et al., "Morpholino and Phosphorothioate Antisense Oligomers Compared in Cell-Free and In-Cell Systems," Antisense & Nucleic Acid Drug Development, vol. 7, pp. 63-70, (1997). Abstract only.
Summerton et al., "Morpholino Antisense Oligomers: The Case for an RNase H-Independent Structural Type," Biochim et. Biophys. Acta, vol. 1489, pp. 141-158, (1999). Abstract only.
Summerton, "Morpholino Antisense Oligomers: Design, Preparation, and Properties," Antisense Nucleic Acid Drug Development, vol. 7(3), pp. 187-195, (1997). Abstract only.

Suwanmanee et al., "Restoration of Human β-Globin Gene Expression in Murine and Human IVS2-654 Thalassemic Erythroid Cells by Free Uptake of Antisense Oligonucleotides," Molecular Pharmacology, vol. 62(3), pp. 545-553, (2002).
Szabo et al., "A Deletion in the Myostatin Gene Cause the Compact (Cmpt) Hypermuscular Mutation in Mice," Mamm Genome, vol. 9, pp. 671-672, (1998).
Tries et al., "GDF-8 Propeptide Binds to GDF-8 and Antagonizes Biological Activity by Inhibiting GDF-8 Receptor Binding," Growth Factors, vol. 18, pp. 251-259, (2001).
Thomas et al., "Myostatin, A Negative Regulator of Muscle Growth, Functions by Inhibiting Myoblast Proliferation," J Biol Chem, vol. 275, pp. 40235-40243, (2000).
Todorovska et al., "Design and Application of Diabodies, Triabodies and Tetrabodies for Cancer Targeting," Journal of Immunological Methods, vol. 248(1), pp. 47-66, (2001).
Toulme et al., "Targeting RNA Structures by Antisense Oligonucleotides," Biochimie, vol. 78(7), pp. 663-673, (1996). Abstract only.
Uhlmann et al., "Anitsense Oligomers: A New Therapeutics Principle," Chemical Reviews, vol. 90(4), pp. 544-584, (1990).
Van Deutekom et al., "Local Dystrophin Restoration with Antisense Oligonucleotide PRO051," N Engl J Med, vol. 357, pp. 2677-2686, (2007).
Van Deutekom et al., "Antisense-Mediated Exon Skipping as a Gene Correction Therapy for Duchenne Muscular Dystrophy," Journal of the Neurological Sciences, vol. 199, pp. S75-S76, (2002).
Van Deutekom et al., "Advances in Duchenne Muscular Dystrophy Gene Therapy," Nat Rev Genet, vol. 4, pp. 774-783, (2003).
Verhaart et al., "Gene Therapy for Duchenne Muscular Dystrophy," Current Opinion in Neurology, vol. 25(5), pp. 588-596, (2012).
Vincent et al., "Long-Term Correction of Mouse Dystrophic Degeneration by Adenovirus-Mediated Transfer of a Minidystrophin Gene," Nature Genetics, vol. 5, pp. 130-134, (1993).
Wagner et al., "A Phase I/IItrial of MYO-029 in Adult Subjects with Muscular Dystrophy," Ann Neurol, vol. 63, pp. 561-571, (2008).
Wallace et al., "Epidemiology of Weight Loss in Humans with Special Reference to Wasting in the Elderly," International Journal of Cardiology, vol. 85(1), pp. 15-21, (2002). Abstract only.
Weinstein et al., "RNAi Nanomedicines: Challenges and Opportunities within the Immune System," Nanotechnology, vol. 21, p. 232001, (2010).
Wengel et al., "LNA (Locked Nucleic Acids): Synthesis and High-Affinity Nucleic Acid Recognition," Chemical Communications, Issue 4, pp. 455-456, (1998).
Wengel et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, vol. 54(14), p. 3607-3630, (1998).
Wengel et al., "Synthesis of 3'-C- and 4'-C-Branched Oligodeoxynucleotides and the Development of Locked Nucleic Acid (LNA)," Accounts of Chemical Research, vol. 32(4), p. 301, (1999).
Whittemore et al., "Inhibition of Myostatin in Adult Mice Increases Skeletal Muscle Mass and Strength," Biochemical and Biophysical Research Communications, vol. 300, pp. 965-971, (2003).
Williams, S.A., "Cationic Lipids Reduce Time and Dose of C-Myc Antisense Oligodeoxynucleotides Required to Specifically Inhibit Burkitt's Lymphoma Cell Growth," Leukemia, vol. 10(12), pp. 1980-1989, (1996).
Williams et al., "A Single Intra-Articular Injection of Liposomally Conjugated Methotrexate Suppresses Joint Inflammation in Rat Antigen-Induced Arthritis," British Journal of Rheumatology, vol. 35(8), pp. 719-724, (1996).
Wilton et al., "Antisense Oligonucleotides in the Treatment of Duchenne Muscular Dystrophy: Where are we now?" Neuromuscular Disorders, vol. 15, pp. 399-402, (2005).
Wilton et al., "Improved Antosense Oligonucleotide Induced Exon Skipping in the Mdx Mouse Model of Muscular Dystrophy," Journal of Gene Medicine, vol. 4, pp. 644-654, (2002).
Wilton et al., "Antisense Oligonucleotide-Induced Exon Skipping Restores Dystrophin Expression In Vitro in a Canine Model of DMD," Gene Therapy, vol. 13, pp. 1373-1381, (2006).

(56) References Cited

OTHER PUBLICATIONS

Wu et al., "Receptor-Mediated In Vitro Gene Transformation by a Soluble DNA Carrier System," Journal of Biological Chemistry, vol. 262, pp. 4429-4432, (1987).

Wu et al., "Octa-Guanidine Morpholino Restores Dystrophin Expression in Cardiac and Skeletal Muscles and Ameliorates Pathology in Dystrophic Mdx Mice," Molecular Therapy, vol. 17, pp. 864-871, (2009).

Xu et al., "Postnatal Overexpression of the CT GalNAc Transferase Inhibits Muscular Dystrophy in MDX Mice Without Altering Muscle Growth or Neuromuscular Development: Evidence for a Utrophin-Independent Mechanism," Neuromuscular Disorders, vol. 17, pp. 209-220, (2007).

Yamada et al., "Synthesis of 2'-O-[2-(Methylcarbamoyl)Ethyl]Ribonucleosides Using Oxa-Michael Reaction and Chemical and Biological Properties if Oligonucleotide Derivatives Incorporating These Modified Ribonucleosides," Journal of Organic Chemistry, vol. 76(9), pp. 3042-3053, (2011).

Yang et al., "A Retrovirus-Based System to Stably Silence GDF-8 Expression and Enhance Myogenic Differentiation in Human Rhabdomyosarcoma Cells," Journal of Gene Medicine, vol. 10, pp. 825-833, (2008).

Yarasheski et al., "Serum Myostatin-Immunoreactive Protein is Increased in 60-92 Year Old Women and Men with Muscle Wasting," Journal of Nutrition, Health, Aging, vol. 6(5), pp. 343-348, (2002). Abstract only.

Yoo et al., "2'-O-Methyl-Modified Phosphorothioate Antisense Oligonucleotides have Reduced Non-Specific Effects In Vitro," Nucleic Acids Research, vol. 32(6), pp. 2008-2016, (2004).

Zamecnik et al., "Inhibition of Rous Sarcoma Virus Replication and Cell Transformation by a Specific Oligodeoxynucleotide," Proceedings of the National Academy of Sciences USA, vol. 75, pp. 280-284, (1978).

Zhang et al., "Computational Definition of Sequence Motifs Governing Constitutive Exon Splicing," Genes & Development, vol. 18, pp. 1241-1250, (2004).

Zhang et al., "Computational Searches for Splicing Signals," Methods, vol. 37, pp. 292-305, (2005).

Zhu et al., "Dominant Negative Myostatin Produces Hypertrophy without Hyperplasia in Muscle," FEBS Letters, vol. 474, pp. 71-75, (2000).

Zhu et al., "Evidence for Human Immunodeficiency Virus Type 1 Replication In Vivo in CD14(+) Monocytes and its Potential Role as a Source of Virus in Patients on Highly Active Antiretroviral Therapy," Journal of Virology, vol. 76(2), pp. 707-716, (2002).

Zimmers et al., "Induction of Cachexia in Mice by Systemically Administered Myostatin," Science, vol. 296(5572), pp. 1486-1488, (2002). Abstract only.

Zollinger et al., "Meningococcal Vaccines—Present and Future," Transactions of Royal Soc of Tropical Medicine and Hygiene, vol. 85(1), pp. 37-43, (1991). Abstract only.

USPTO; Final Office Action dated Nov. 13, 2019 in the U.S. Appl. No. 15/559,257.

USPTO; Notice of Allowance dated Dec. 26, 2019 in the U.S. Appl. No. 15/986,746.

OLIGOMERS

CROSS-REFERENCE TO RELATED APPLICATIONS

This application is a continuation of U.S. patent application Ser. No. 16/129,680 filed on Sep. 12, 2018 entitled "OLIGOMERS", which is a continuation of U.S. patent application Ser. No. 15/078,029 filed on Mar. 23, 2016, entitled "OLIGOMERS", which is a divisional application of U.S. application Ser. No. 14/504,453 filed on Oct. 2, 2014, entitled "OLIGOMERS", which is a continuation of U.S. patent application Ser. No. 13/644,363 filed on Oct. 4, 2012, entitled "OLIGOMERS", which claims priority to U.S. Provisional Patent Application No. 61/543,145 filed on Oct. 4, 2011 entitled "OLIGOMERS", the disclosures of which are incorporated herein by reference.

FIELD OF THE INVENTION

The present invention relates to oligomers which are capable of causing exon skipping and, in particular, relates to oligomers which are capable of causing exon skipping in the myostatin gene.

BACKGROUND TO THE INVENTION

A range of strategies have been proposed to enhance muscle bulk and strength as a treatment for a number of age-related muscle disorders and various neuromuscular disorders, including muscular dystrophies. Myostatin, a transforming growth factor-β family member, also called growth and differentiation factor-8, is a negative regulator of muscle growth and the myostatin signalling axis has been a major focus in such strategies. Myostatin null or hypomorphic animals are significantly larger than wild-type animals and show a large increase in skeletal muscle mass.[1] The first natural myostatin mutation in humans has also been identified in a young boy.[2] Myostatin blockade, therefore, offers a strategy for counteracting muscle-wasting conditions including Duchenne muscular dystrophy.[3] Delivery of myostatin-inhibiting genes, including growth and differentiation factor-associated serum protein-1 (GASP-1), follistatin-related gene (FLRG), follistatin-344 (FS) and myostatin propeptide, via adeno-associated virus,[4-6] lead to an increase in muscle mass in treated animals, with the greatest increase in FS-treated animals. Use of potentially therapeutic antimyostatin-blocking antibodies of high-binding affinity has proved to be a promising strategy. However, there are some constraints related to the use of antimyostatin antibodies that include difficulty in long-term sustainability, undesirable immune responses, and inhibitory effects not precisely specific to myostatin in regard to muscle growth.[8,9] Significant increase in skeletal muscle mass was also observed using adeno-associated virus vectors to deliver a recombinant myostatin propeptide gene fragment, or by a retrovirus-based RNA interference system (RNAi).[4,6,10] Both approaches have safety concerns of possible genotoxicity, due to uncontrolled vector genome insertion into host chromosomes.[11] The RNAi system faces an additional hurdle in terms of effective delivery of the RNAi molecules into the disease models for clinical studies.[12] RNA-based modulation therapy has the potential to overcome difficulties encountered by conventional gene therapy methods. Antisense oligonucleotides (AOs) are capable of hybridizing to a sense target sequence leading to cleavage of the RNA:DNA hybrid by RNase H which results in downregulation of gene transcription.[13,14] In an alternative approach, antisense-mediated modulation of pre-mRNA splicing has been pioneered by Dominski and Kole.[15] In the first experiments, AOs were aimed at activated cryptic splice sites in the β-globin (HBB) and cystic fibrosis transmembrane conductance regulator (CFTR) genes in order to restore normal splicing in β-thalassemia and cystic fibrosis patients.[15-17] The identification of exon/intron boundaries by the splicing machinery, and therefore inclusion of the exons into the mRNA, is extensively thought to depend on exonic splicing enhancer (ESE) motifs.[18] By masking these ESE sites with sequence-optimized AOs, the targeted exons are no longer recognized as exons, and are spliced out with neighbouring introns. This so-called antisense-induced exon skipping has already been used clinically to partly correct the mutated dystrophin and convert the severe Duchenne muscular dystrophy phenotype into a milder Becker muscular dystrophy phenotype.[19] Clinical trials to determine the safety profile and the efficacy of single intramuscular doses of two different chemistries of AOs, 2'-O-methyl phosphorothioate (2'OMePS) AOs and phosphorodiamidate morpholino oligomers (PMOs) in Duchenne muscular dystrophy patients have recently been completed.[20,21] The treatments were well tolerated by all the patients and the injection of AOs induced the production of dystrophin. 2'OMePS AOs, being negatively charged, are easily delivered in vitro, whereas PMOs are capable of more sustained effect in vivo due to their resistance to enzymatic degradation[22] and owing to their longer sequence, have increased affinity to target.[23] When conjugated with various peptide derivatives, or with dendrimeric octa-guanidine (so-called Vivo-morpholino), PMOs demonstrate a significantly increased delivery in the case of dystrophin skipping.[24,25]

SUMMARY OF THE INVENTION

The inventors have adopted the approach of using AOs with different chemistries, so enhancing their half-lives relative to RNAi molecules, to investigate the outcome of myostatin knockdown by exon skipping. Skipping of exon 2 (374 nucleotides) of myostatin leads to an out-of-phase splicing of exons 1 and 3, and knockdown of myostatin due to truncation of the Open Reading Frame and nonsense-mediated mRNA decay. The data present here constitute a proof-of-principle that oligonucleotide-mediated antisense exon skipping leads to a physiologically significant myostatin knockdown in vitro and in vivo. This type of antisense treatment could thus form part of an effective strategy to improve various muscle-wasting conditions, and along with dystrophin rescue or augmentation, to treat Duchenne muscular dystrophy.

The present invention relates to oligomers which can bind to pre-mRNA produced from the myostatin gene and cause exon skipping during cellular processing of the pre-mRNA.

The present invention provides an oligomer for inducing exon skipping during processing of myostatin pre-mRNA, the oligomer comprising at least 20 contiguous bases of a base sequence selected from the group consisting of:

1) XCXCGACGGGXCXCAAAXAXAXCCAXAGXX; (SEQ ID NO. 1)

2) XGXACCGXCXXXCAXAGGXXXGAXGAGXCX; (SEQ ID NO. 2)

3) CCXGGGXXCAXGXCAAGXXXCAGAGAXCGG; (SEQ ID NO. 3)

4) CAGCCCAXCXXCXCCXGGXCCXGGGAAGGX; (SEQ ID NO. 4)

-continued

5)  XCXXGACGGGXCXGAGAXAXAXCCACAGXX;  (SEQ ID NO. 5)

6)  XGXACCGXCXXXCAXGGGXXXGAXGAGXCX;  (SEQ ID NO. 6)

7)  CCXGGGCXCAXGXCAAGXXXCAGAGAXCGG;  (SEQ ID NO. 7)

8)  XCCACAGXXGGGCXXXXACX;  (SEQ ID NO. 8)

9)  XCXGAGAXAXAXCCACAGXX;  (SEQ ID NO. 9)

10) XCXXGACGGGXCXGAGAXAX;  (SEQ ID NO. 10)

11) XGAXGAGXCXCAGGAXXXGC;  (SEQ ID NO. 11)

12) XXCAXGGGXXXGAXGAGXCX;  (SEQ ID NO. 12)

13) XXGXACCGXCXXXCAXGGGX;  (SEQ ID NO. 13)

14) CAGAGAXCGGAXXCCAGXAX;  (SEQ ID NO. 14)

15) XGXCAAGXXXCAGAGAXCGG;  (SEQ ID NO. 15)

16) CCXGGGCXCAXGXCAAGXXX;  (SEQ ID NO. 16)

17) CXGGGAAGGXXACAGCAAGA;  (SEQ ID NO. 17)

18) XCXCCXGGXCCXGGGAAGGX;  (SEQ ID NO. 18)
    and

19) CAGCCCAXCXXCXCCXGGXC,  (SEQ ID NO. 19)

wherein X is T or U and the oligomer's base sequence can vary from the above sequence at up to two base positions, and wherein the oligomer can bind to a target site in the myostatin pre-mRNA to cause exon skipping.

The oligomers described above cause exon skipping in the myostatin gene. In particular, these oligomers cause exon skipping of exon two of the myostatin gene, i.e. when the myostatin pre-mRNA is processed into mRNA, the oligomers stop exon two from being included in the mRNA.

Without being restricted to any particular theory, it is thought that the binding of the oligomers to the myostatin pre-mRNA interacts with or interferes with the binding of SR proteins to the exon. SR proteins are involved in the splicing process of adjacent exons. Therefore, it is thought that interacting or interfering with the binding of the SR proteins interferes with the splicing machinery resulting in exon skipping.

The base "X" in the above base sequences is defined as being thymine (T) or uracil (U). The presence of either base in the sequence will still allow the oligomer to bind to the pre-mRNA of the myostatin gene as it is a complementary sequence. Therefore, the presence of either base in the oligomer will cause exon skipping. The base sequence of the oligomer may contain all thymines, all uracils or a combination of the two. One factor that can determine whether X is T or U is the chemistry used to produce the oligomer. For example, if the oligomer is a phosphorodiamidate morpholino oligonucleotide (PMO), X will be T as this base is used when producing PMOs. Alternatively, if the oligomer is a phosphorothioate-linked 2'-O-methyl oligonucleotide (2'OMePS), X will be U as this base is used when producing 2'OMePSs. Preferably, the base "X" is only thymine (T).

The advantage provided by the oligomer is that it causes exon skipping. Preferably, the oligomer causes an exon skipping rate of at least 40%, i.e. exon two will be skipped 40% of the time. More preferably, the oligomer causes an exon skipping rate of at least 50%, more preferably still, at least 60%, even more preferably, at least 70%, more preferably still, at least 75%, more preferably, at least 80%, even more preferably, at least 85%, more preferably still, at least 90%, even most preferably, at least 95%, more preferably, at least 98% and even more preferably, at least about 99%. Exon skipping can be measured by transfection (leashed or unleashed: concentration between 50 and 500 nM) into cultured human myoblast cells (e.g., using a transfection reagent such as Lipofectamine2000™), and evaluation of skipped and unskipped mRNAs by electrophoretic densitometric analysis of RTPCR reaction products.

The oligomer can be any type of oligomer as long as it has the selected base sequence and can bind to a target site of the myostatin pre-mRNA to cause exon skipping. For example, the oligomer can be an oligodeoxyribonucleotide, an oligoribonucleotide, a phosphorodiamidate morpholino oligonucleotide (PMO) or a phosphorothioate-linked 2'-O-methyl oligonucleotide (2'OMePS). Preferably, the oligomer is a PMO or a 2'OMePS. In one embodiment, the oligomer is a PMO. The advantage of a PMO is that it has excellent safety profiles and appears to have longer lasting effects in vivo compared to 2'OMePS oligonucleotides. Preferably, the oligomer is isolated so that it is free from other compounds or contaminants.

The base sequence of the oligomer can vary from the selected sequence at up to two base positions. If the base sequence does vary at two positions, the oligomer will still be able to bind to the myostatin pre-mRNA to cause exon skipping. Preferably, the base sequence of the oligomer varies from the selected sequence at up to one base position and, more preferably, the base sequence does not vary from the selected sequence. The less that the base sequence of the oligomer varies from the selected sequence, the more efficiently it binds to the target site in order to cause exon skipping.

The oligomer is at least 20 bases in length. Preferably, the oligomer is at least 25 bases in length. In some embodiments, the oligomer may be at least 28 bases in length or at least 30 bases in length. Preferably, the oligomer is no more than 40 bases in length. In some embodiments, the oligomer may be no more than 35 bases in length or no more than 32 bases in length. Preferably, the oligomer is between 20 and 40 bases in length. More preferably, the oligomer is between 25 and 35 bases in length. In some embodiments, the oligomer is between 28 and 32 bases in length, between 29 and 31 bases in length, or about 30 bases in length. It has been found that an oligomer which is 30 bases in length causes efficient exon skipping. If the oligomer is longer than 40 bases in length, the specificity of the binding to the target site may be reduced. If the oligomer is less than 20 bases in length, the exon skipping efficiency may be reduced.

In some embodiments, the oligomer comprises at least 20 contiguous bases of a base sequence selected from the group consisting of SEQ ID NOS. 1-7, wherein the oligomer's base sequence can vary from SEQ ID NOS. 1-7 at up to two base positions.

In other embodiments, the oligomer comprises at least 20 contiguous bases of a base sequence selected from the group consisting of SEQ ID NOS. 1-4, wherein the oligomer's base sequence can vary from SEQ ID NOS. 1-4 at up to two base positions.

In the above embodiments relating to SEQ ID NOS. 1-7 and SEQ ID NOS. 1-4, the oligomer preferably comprises at least 25 contiguous bases of the base sequences. More preferably, the oligomer comprises at least 28 contiguous bases of the base sequences. In some embodiments, the oligomer comprises 30 contiguous bases of the base sequences, i.e. the oligomer comprises the base sequences of SEQ ID NOS. 1-7 or SEQ ID NOS. 1-4. In the embodiments described in this paragraph, the oligomer's base sequence can still vary from SEQ ID NOS. 1-7 or SEQ ID NOS. 1-4 at up to two base positions.

The oligomer may be conjugated to or complexed with various distinct chemical entities. For example, the oligomer may be conjugated to or complexed with a targeting protein in order to target the oligomer to, for example, muscle tissue. If the oligomer is conjugated to an entity, it may be conjugated directly or via a linker. In one embodiment, a plurality of oligomers may be conjugated to or complexed with a single entity. For example, the oligomer may be conjugated to octa-guanidine dendrimers. Alternatively, an arginine-rich cell penetrating peptide (CPP) can be conjugated to or complexed with the oligomer. In particular, (R-Ahx-R)$_4$AhxB can be used, where Ahx is 6-aminohexanoic acid and B is beta-alanine (Moulton H M et al. (2007) *Biochem. Soc. Trans.* 35: 826-8.), or alternatively (RXRRBR)$_2$XB (SEQ ID NO: 36) can be used.[26] These entities have been complexed to known dystrophin exon-skipping oligomers which have shown sustained skipping of dystrophin exons in vitro and in vivo.

Alternatively, a range of nanoparticle systems can be used to deliver the oligomers[74].

In another aspect, the present invention provides a vector for inducing exon skipping during processing of myostatin pre-mRNA, the vector encoding an oligomer of the invention, wherein when the vector is introduced into a cell (e.g. a human cell), the oligomer is expressed. For example, it is possible to express antisense sequences in the form of a gene, which can thus be delivered on a vector. One way to do this would be to modify the sequence of a U7 snRNA gene to include an antisense sequence according to the invention. The U7 gene, complete with its own promoter sequences, can be delivered on an adeno-associated virus (AAV) vector, to induce bodywide exon skipping. Similar methods to achieve exon skipping, by using a vector encoding an oligomer of the invention, would be apparent to one skilled in the art.

The present invention also provides a pharmaceutical composition for inducing exon skipping during processing of myostatin pre-mRNA, the composition comprising an oligomer as described above or a vector as described above and a pharmaceutically acceptable carrier, adjuvant or vehicle.

Pharmaceutical compositions of this invention comprise an oligomer of the present invention, and pharmaceutically acceptable salts, esters, salts of such esters, or any other compound which, upon administration to a subject (e.g. a human), is capable of providing (directly or indirectly) the biologically active oligomer thereof, with a pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally, intradermally or via an implanted reservoir. Oral administration or administration by injection is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intraarticular, intrasynovial, intrasternal, intrathecal, intralesional and intracranial injection or infusion techniques. Preferably, the route of administration is by injection, more preferably, the route of administration is intramuscular, intravenous or subcutaneous injection and most preferably, the route of administration is intravenous or intramuscular injection.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent, dispersant or similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The pharmaceutical composition of the invention may also comprise an additional biologically active agent. For example, where the composition is for ameliorating Duchenne muscular dystrophy, the composition may comprise an oligomer for causing exon skipping in the dystrophin gene. Such oligomers are described, for example, in U.S. application Ser. No. 12/556,626.

The oligomers of the invention are for use in therapy and, in particular, for use in inducing exon skipping during processing of myostatin pre-mRNA.

The present invention also provides a method of inducing exon skipping during processing of myostatin pre-mRNA in a patient (e.g. a human patient), the method comprising administering a therapeutically effective amount of the oligomer of the invention or the vector of the invention to the patient such that exon skipping during processing of myostatin pre-mRNA is induced.

In the above method, the oligomers can be used to increase or maintain muscle mass, or to slow the degeneration of muscle mass. In particular, musculoskeletal muscle mass can be increased or maintained, or its degeneration slowed. For example, the method can be for ameliorating muscle wasting conditions such as degenerative muscular disorders, including various forms of muscular dystrophy. Degenerative muscular disorders such as various forms of muscular dystrophies can actually be fatal at an early age of mid to late twenties. Muscle wasting conditions that can be ameliorated using the oligomers include muscular dystrophy such as Becker's muscular dystrophy, congenital muscular dystrophy, Duchenne muscular dystrophy, distal muscular dystrophy, Emery-Dreifuss muscular dystrophy, facioscapulohumeral muscular dystrophy (FSHD), limb-girdle muscular dystrophy, myotonic muscular dystrophy and oculopharyngeal muscular dystrophy. In one embodiment, the method is for ameliorating Duchenne muscular dystrophy (DMD). Other conditions that could be ameliorated by myostatin oligomers include cachexia (muscle loss due to for example, cancer, chronic obstructive pulmonary disease (COPMD) and HIV/AIDS), sarcopenia (muscle loss due to natural old age), muscle atrophy (muscle loss in denervating conditions such as motorneuron disease, and spinal muscular atrophy). In addition, myostatin knockdown by oligomers and the ensuing increased muscle bulk may also have the potential to counteract insulin-resistance in diabetes and obesity-related metabolic syndromes.

In some embodiments of the invention, another biologically active agent may also be administered in a therapeutically effective amount. For example, where the method is for ameliorating DMD, antisense oligomers for causing exon skipping in the dystrophin gene may also be administered. Such oligomers are described, for example, in U.S. application Ser. No. 12/556,626.

DETAILED DESCRIPTION OF THE INVENTION

The present invention will now be described in detail, by way of example only, with reference to the accompanying figures in which:

FIGS. 1A-1B: Bioinformatics analysis, design, and evaluation in C2C12 muscle cells of specific AOs predicted to induce skipping of myostatin exon 2. (FIG. 1A) Results from three algorithms used to identify ESE sequences for designing of exon skipping AOs targeting exon 2 of the mouse myostatin gene. The ESE Finder analysis shows the location and values above threshold for SR protein-binding motifs, SF2/ASF, SF2/ASF (BRCA 1), SC35, SRp40, and SRp55 which are shown as vertical bars above the sequence of exon 2. The Rescue ESE analysis shows the position of possible exonic splicing enhancer sites by black horizontal lines parallel to the sequence of exon 2. The PESX analysis shows the location of ESEs as light gray horizontal lines, and exon splicing silencers (ESSs) as dark gray horizontal lines. The bold horizontal laddered black lines represent the sequence of the 20-mer 2'OMePSs which were obtained after aligning the outputs from the three algorithms. (FIG. 1B) Comparison of efficacy of different 2'OMePS oligomers to induce skipping of exon 2 in myostatin mRNA from C2C12 cell cultures. RT-PCR was performed on 1 µg mRNA from C2C12 cells treated with 12 different 2'OMePS oligomers at 250 nmol/l. Transfections were performed in duplicates and the nested RT-PCR products were loaded on 1.2% agarose gel as follow: Tracks 1 and 2: oligomer A1; Tracks 3 and 4: oligomer A2; Tracks 5 and 6: oligomer A3; Tracks 9 and 10: oligomer B1; Tracks 11 and 12: oligomer B2; Tracks 13 and 14: oligomer B3; Tracks 15 and 16: oligomer C1; Tracks 17 and 18: oligomer C2; Tracks 19 and 20: oligomer C3; Tracks 23 and 24: oligomer D1; Tracks 25 and 26: oligomer D2; Tracks 27 and 28: oligomer D3; Tracks 7, 8, 21 and 22: controls with transfection reagent Lipofectamine 2000 alone, but no AO: Size Marker used is Hyper ladder IV. 2'OMePS, 2'O-methyl phosphorothioate RNA; AO, antisense oligonucleotide; bp, base pairs; ESE, exonic splicing enhancer; RT-PCR, reverse transcriptase-PCR.

Figure 2:
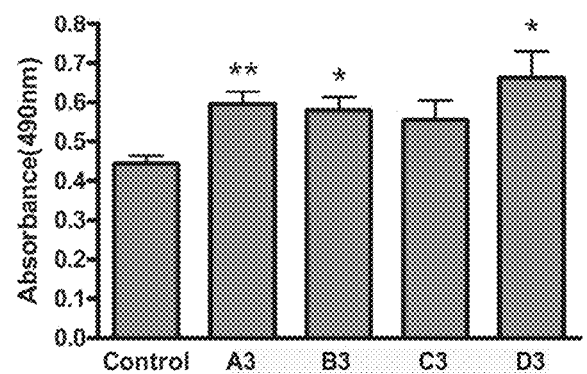

FIG. 2: Antisense-induced myostatin exon 2 skipping with 2'OMePS oligomers leads to an increase in C2C12 cell proliferation. C2C12 cells were treated with a range of 2'OMePS oligomers along with lipofectamine 2000 (LF2000), and assayed 24 hours later for cell proliferation by lactic dehydrogenase assay. Treatment with 2'OMePS oligomers A3, B3, and D3 resulted in significant increases in the number of cells after 24 hours compared to the cultures treated with only transfection reagent LF2000 but no AO. C3 did not induce a substantial change. (t-test analysis, n=6; *P<0.05; **P<0.01). 2'OMePS, 2'O-methyl phosphorothioate RNA.

Figure 3:
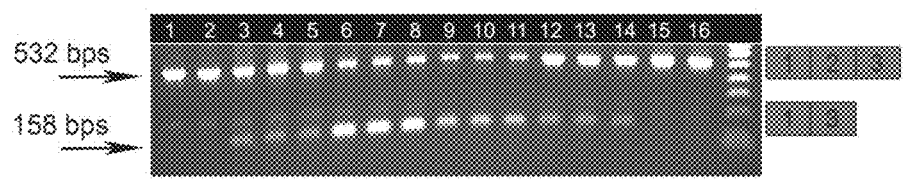

FIG. 3: Exon skipping in mouse following intramuscular injection of 2'OMePS oligomers targeting myostatin exon 2. Oligomers A2 and B3 (3 nmol) were administered by a single intramuscular injection into the tibialis anterior (TA) muscles of mice. Two and four weeks later, muscles were recovered, and RNA extracted and analyzed for the presence of myostatin exon 2 skipping by RT-PCR. Agarose ethidium bromide gel electrophoresis is shown for the products of RT-PCR analysis: The upper and lower bands correspond to the normal exon 1, 2, and 3 product (532 bp) and the exon 2 skipped product (158 bp), respectively which were verified by sequencing (data not shown). The faint shadow band of intermediate migration in some tracks was found upon sequencing to correspond to a product containing a partial sequence of exon 2 due to a cryptic 3' splice site 296 nt downstream of the correct one. Tracks 1 and 2: 14 days control; Tracks 3-5: 14 days A2-treated; Tracks 6-8: 28 days A2-treated; Tracks 9-11; 14 days B3-treated; Tracks 12-14: 28 days B3-treated; Tracks 15 and 16: 28 days control. Densitometric evaluation of the skipped and unskipped bands showed that after 14 days, A2 gave 25.6% and B3 54.6% skipping, and after 28 days, A2 gave 48.6% and B3 24.5% skipping. 2'OMePS, 2'O-methyl phosphorothioate RNA; bps, base pairs; nt, nucleotides; RT-PCR, reverse transcriptase-PCR.

Figure 4:
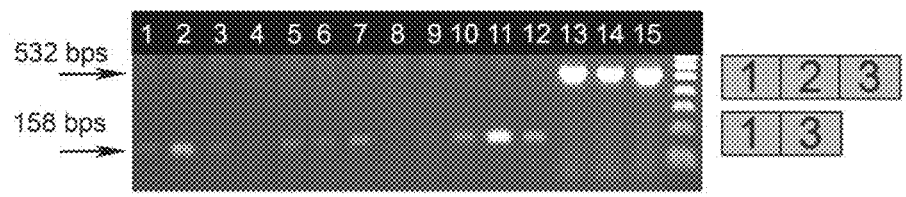

FIG. 4: Myostatin exon 2 skipping in C2C12 cell culture following treatment with a range of leashed-PMO lipoplexes. C2C12 cell cultures treated with a range of leashed PMOs in lipoplex form with LF2000 exhibited skipping of exon 2 in myostatin mRNA. RT-PCR was performed on 1 μg mRNA from C2C12 cells treated with 250 nmol/l PMOs (designed on the basis of the most effective 2'OMePS sequences: A3, B3, C3, and D3) over a period of 24 hours. Transfections were performed in triplicate and RT-PCR products were loaded on 1.2% agarose gel as follows: Tracks 1-3: PMO-A; Tracks 4-6: PMO-B; Tracks 7-9: PMO C; Tracks 10-12: PMO-D; Tracks 13-15: LF2000-treated control; bps, base pairs; LP2000, lipofectamine 2000; PMO, phosphorodiamidate morpholino oligomers; RT-PCR, reverse transcriptase-PCR.

Figure 5:
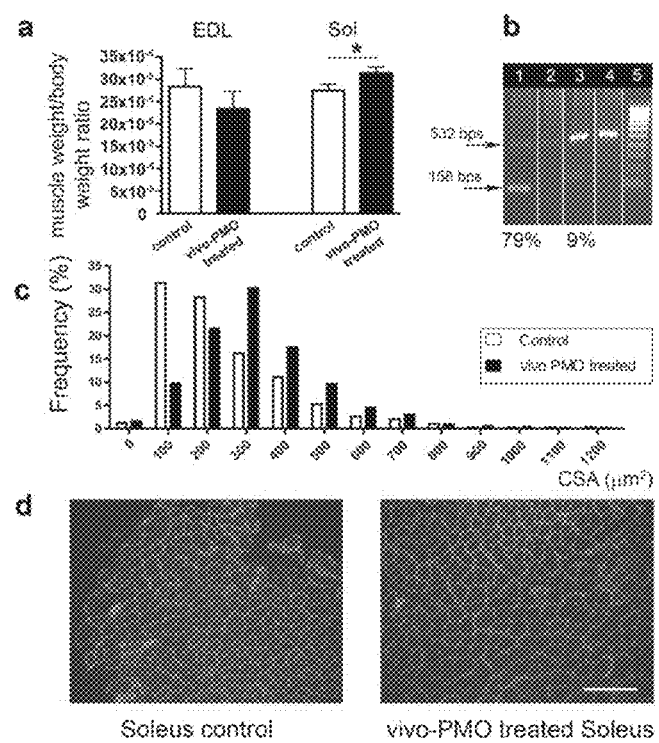

FIG. 5: Systemic injection of PMO conjugated to octa-guanidine dendrimer (Vivo-PMO) results in myostatin exon skipping associated with a significant increase in muscle mass and myofiber size. Mice were treated with 6 mg/kg of Vivo-PMO-D3 by five weekly intravenous injections, and muscles harvested for RNA extraction and immunohistology 10 days later. (a) Weight of soleus and EDL muscle after treatment. Weights of soleus muscles were significantly increased (t-test, P<0.034; n=6) whereas weights of EDL muscles showed no significant change. (b) RT-PCR was carried out on 1 μg RNA from soleus and EDL muscles and products resolved on a 1.2% agarose gel. Track 1: Vivo-PMO treated soleus; Track 2: control soleus; Track 3: Vivo-PMO treated EDL; Track 4: control EDL. (c) Distribution of myofiber sizes (CSA) in vivo-PMO treated (black bars) and control (open bars) soleus muscles. (d) Representative dystrophin immunohistology indicating increased myofibre CSA in vivo-PMO treated compared to control soleus muscle cryosections. Bar=500 am. CSA, cross-sectional area; EDL, extensor digitorum longus; PMO, phosphorodiamidate morpholino oligomers; RT-PCR, reverse transcriptase-PCR.

INTRODUCTION

As stated above, the inventors have adopted the approach of using AOs with different chemistries, so enhancing their half-lives relative to RNAi molecules, to investigate the outcome of myostatin knockdown by exon skipping. Skipping of exon 2 (374 nucleotides) of myostatin was predicted to lead to an out-of-phase splicing of exons 1 and 3, and knockdown of myostatin due to truncation of the Open Reading Frame and nonsense-mediated mRNA decay. The data present below constitute a proof-of principle that oligonucleotide-mediated antisense exon skipping leads to a physiologically significant myostatin knockdown in vitro and in vivo. This type of antisense treatment could thus potentially form part of an effective strategy to improve various muscle-wasting conditions, and along with dystrophin rescue or augmentation, to treat Duchenne muscular dystrophy.

Example 1

Materials and Methods
Bioinformatics Analysis of the Myostatin Gene to Design AOs Reagents.

Three different bioinformatics algorithms namely ESE Finder, PESX, and Rescue ESE were used to design antisense reagents. Results from the three algorithms were merged to define ESE sites and used to identify the regions of the myostatin exon 2, which are expected to be optimal targets for exon skipping antisense reagents. A set of 12 antisense reagents of 2'O-methyl RNA (2'OMePS) chemistry were designed to target four different ESE-rich regions of exon 2 of myostatin (FIG. 1A).

AO Reagents.

The 12 2'OMePS oligomers tested were obtained from Eurogentec (SA, Seraing, Belgium). The sequences of the 2'OMePS are as follows:

```
                            (SEQ ID NO: 20)
GDF8/A1:     TCCACAGTTGGGCTTTTACT (SEQ ID NO: 21)
GDF8/A2:     TCTGAGATATATCCACAGTT (SEQ ID NO: 22)
GDF8/A3:     TCTTGACGGGTCTGAGATAT (SEQ ID NO: 23)
GDF8/B1:     TGATGAGTCTCAGGATTTGC (SEQ ID NO: 24)
GDF8/B2:     TTCATGGGTTTGATGAGTCT (SEQ ID NO: 25)
GDF8/B3:     TTGTACCGTCTTTCATGGGT (SEQ ID NO: 26)
GDF8/C1:     CAGAGATCGGATTCCAGTAT (SEQ ID NO: 27)
GDF8/C2:     TGTCAAGTTTCAGAGATCGG (SEQ ID NO: 28)
GDF8/C3:     CCTGGGCTCATGTCAAGTTT (SEQ ID NO: 29)
GDF8/D1:     CTGGGAAGGTTACAGCAAGA (SEQ ID NO: 30)
GDF8/D2:     TCTCCTGGTCCTGGGAAGGT (SEQ ID NO: 31)
GDF8/D3:     CAGCCCATCTTCTCCTGGTC
```

PMOs were designed based on the 2'OMePS sequences. A total of four PMOs were tested and were obtained from Gene Tools (Philomath, Oreg.). PMO sequences are as follows:

| | (SEQ ID NO: 32) |
|---|---|
| Mstn A: | TCTTGACGGGTCTGAGATATATCCACAGTT |

| | (SEQ ID NO: 33) |
|---|---|
| Mstn B: | TGTACCGTCTTTCATGGGTTTGATGAGTCT |

| | (SEQ ID NO: 34) |
|---|---|
| Mstn C: | CCTGGGCTCATGTCAAGTTTCAGAGATCGG |

| | (SEQ ID NO: 35) |
|---|---|
| Mstn D: | CAGCCCATCTTCTCCTGGTCCTGGGAAGGT |

PMOs conjugated to octa-guanidine dendrimers (so-called Vivo-PMOs) were purchased from Gene Tools.

Cell Culture and Transfection of C2C12 Cells with the Designed Antisense Reagents.

C2C12 mouse myoblasts were maintained in Dulbecco's modified Eagle's medium (Sigma-Aldrich, Poole, UK) containing 10% fetal calf serum (Sigma-Aldrich), 4 mmol/l l-glutamine, 100 U/ml penicillin and 100 µg/ml streptomycin at 37° C. and 8% $CO_2$. Cells were split every 24 hours to prevent differentiation. Cells were detached by incubating them with 0.15% trypsin-phosphate-buffered saline for 1 minute at 37° C., and seeded at a density of 1.5×105 cells/well of a 6-well plate. The antisense reagents of 2'OMePS chemistry were transfected at 250 nmol/l into C2C12 cells using Lipofectamine 2000 (Invitrogen, Paisley, UK). Controls contained Lipofectamine 2000 but no antisense reagent. PMOs were leashed to complementary stretches of negatively charged DNA (obtained from MWG, Ebersberg, Germany) for efficient in vitro delivery,[24] using Lipofectamine 2000 as transfection reagent. All transfections were performed in Dulbecco's modified Eagle's medium containing 2 mmol/l glutamine (without serum and antibiotics) and after 3-4 hours of transfection, the medium was replaced with full growth medium containing serum as well as antibiotics. The transfections were performed in duplicate and the experiment repeated twice.

RT-PCR Analysis of Myostatin Exon Skipping.

For in vitro experiments, 24 hours after transfection, RNA was extracted from each well using QIAshredder/RNeasy extraction kit (Qiagen, Crawley, UK). For in vivo experiments, RNA was extracted from blocks using TRIzol reagent (Invitrogen, Scotland, UK). One microgram of RNA was reverse transcribed and resulting complementary DNA amplified using specific primers obtained from MWG, using the Genescript kit (Genesys, Camberley, UK). One micro litre of PCR products obtained was used as a template for nested PCR. Sequences of the primers and details of the PCR protocols used are available on request. The products from nested PCR were separated on 1.2% agarose gel in Tris-borate/EDTA buffer and Hyper Ladder IV (Bioline, London, UK) was used as the marker. Densitometric analysis of the agarose gels was carried out using Gene Tools 3.05 (Syngene, Cambridge, UK) and percentage skipping expressed as amount of skipped product seen relative to total PCR products detected.

In Vitro Cell Proliferation Assay.

A proliferation assay using Cell Titer 96 Aqueous One Solution Cell Proliferation assay (Promega, Madison, Wis.) was performed, as reported by Cory et al.,[75] on cells transfected with different 2'OMePS. Briefly, 24 hours after seeding, the growth media was replaced with serum-free media and cells incubated at 37° C. After 24 hours of subjecting cells to serum-free media, 15 µl of assay reagent was added to 75 µl cells in a 96-well plate. Plates were read at 490 nm. Statistical analysis on the data from the proliferation assay was performed using the individual t-test.

Treatment of Mice with PMOs and Vivo-PMOs.

For all the in vivo experiments, animals (MF1 or C57B110) were bought from Harlan (Blacktown, UK) and in-house maintained, and in vivo experimentation conducted under statutory Home Office recommendation, regulatory, ethical and licensing procedures and under the Animals (Scientific Procedures) Act 1986 (project licence PPL 70/7008). For intramuscular delivery, mice were anaesthetized and injected with 3 nmol of 2'OMePS (in 25 µl normal saline) into each of the TA muscles. Control animals were injected with normal saline. Whole body weights were measured weekly. TAs of treated and control mice were excised postmortem after 2 weeks (n=4) and 4 weeks (n=4). Weights were measured and the muscles frozen in isopentane cooled with liquid nitrogen. For the systemic administration, C57BL10 mice were injected intravenously with 6 mg/kg of Vivo-PMO-D (Gene Tools) diluted in 200 µl of normal saline, every week for 5 weeks. Weights were measured weekly and various muscles from treated and control mice were harvested 10 days after the last injection. Cryosectioning was performed at 10 levels through the muscle.

Immunocytochemistry and Morphometry.

Hematoxylin and eosin staining was used to estimate the muscles size. For the estimation of fibre size and distribution, laminin staining was performed. Laminin antibody from Sigma-Aldrich (Dorset, UK) was used as primary antibody, with biotinylated anti-rabbit immunoglobulin G (Dako, Glostrup, Denmark) as secondary antibody. Finally sections were stained with DAB (Vector Laboratories, Burlingame, Calif.) and slides mounted in DPX (VWR International, Poole, England) after appropriate washings. Immunostaining was also carried out with Dystrophin antibody. For this, H12 Polyclonal Rabbit antibody was used as primary antibody, and Alexa fluor goat anti-rabbit 568 (fluorescein isothiocyanate) (Invitrogen, Paisley, Oreg.) was used as secondary antibody. Slides were mounted in Vectashield mounting medium with DAPI (Vector Laboratories) after appropriate washings with phosphate-buffered saline-Tween. CSA of muscle fibres was measured using SigmaScan Pro 5.0.0 (Systat Software, London, UK).

Results

Bioinformatics Analysis and Design of Specific AOs Predicted to Induce Skipping of Myostatin Exon 2.

Bioinformatics analysis of exon 2 of myostatin was performed using three bioinformatics tools, ESE finder,[27,28] PESX,[29,30] and Rescue ESE,[31] to identify and locate ESEs and exonic splicing suppressor or silencer motifs. The output of these algorithms is displayed in FIG. 1A. A series of overlapping AOs were designed and synthesized as 2'OMePSs and PMOs to span sequences where clusters of ESEs which were predicted by one or more of the programs coincide.

High Levels of Myostatin Exon 2 Skipping in C2C12 Cell Culture Following Treatment with a Range of AOs.

In order to verify the efficiency of these AO target sequences, C2C12 muscle cell cultures were transfected with the 2'OMePS oligomers, and nested reverse transcriptase-PCR (RT-PCR) for skipping of myostatin performed on the RNA extracted from transfected and control cells. A representative horizontal agarose gel electrophoresis separation of products obtained is shown in FIG. 1B. The level of skipping produced by each AO at 250 nmol/l was determined semiquantitatively using densitometric analysis.[31] All of the designed 2'OMePSs were observed to induce myostatin exon 2 skipping in C2C12 cultures but at various levels of relative efficiency. A2 and A3 induced almost 100% skipping; B3 (74%), C3 (41%), and D3 (48%) also induced a considerable level of skipping. The nature of putative antisense-induced PCR exon1-exon3 splicing product was confirmed by sequencing the products.

Antisense-Induced Myostatin Exon 2 Skipping and Myostatin Knockdown Leads to an Increase in C2C12 Cell Proliferation.

In order to verify that AO-mediated myostatin exon 2 skipping and knockdown, lead to a significant biological response, the autocrine activity of myostatin on C2C12 cell proliferation was evaluated following treatment of cultures with 2'OMePSs targeting myostatin exon 2. The cell proliferation assay was based on determination of lactic dehydrogenase activity of metabolically active cells. The results of the proliferation assay clearly showed a remarkable difference in cell proliferation in C2C12 cells treated with myostatin exon 2 AOs compared to mock-transfected control cells (FIG. 2). Statistical analysis of the data using individual paired t-tests showed that oligomers A3 (P=0.0031), B3 (P=0.0055) and D3 (P=0.0115) induced a significant increase in cell proliferation, as compared to mock transfected control cells. Oligomer C3 (P=0.0534) did not produce a statistically significant change.

Demonstration of Exon Skipping in Mouse Following Intramuscular Injection of 2'OMePS Oligomers Targeting Myostatin Exon 2.

On the basis of RT-PCR results obtained from the in-vitro studies, two 2'OMePS oligomers (A2 and B3) were selected to evaluate their ability to induce efficient exon skipping in vivo. The 2'OMePS oligomers (3 nmol) were administered by intramuscular injection into tibialis anterior (TA) muscles of mice. Two and four weeks after the injections, muscles were recovered, weighed, RNA extracted and analyzed for the presence of myostatin exon 2 skipping by RT-PCR. Both reagents (A2 and B3) induced significant level of myostatin exon 2 skipping at either the 2 weeks and 4 weeks time points after a single 2'OMePS oligomer administration (FIG. 3). Densitometric quantification of full-length and skipped product bands from the RT-PCR analyses of RNA was performed to detect which of the two 2'OMePSs tested was the more efficient in vivo. Oligomer A2 gave 25.6% skipping, and B3 gave 54.6% skipping at the 2 weeks time point. However, after 4 weeks, A2 gave 48.6% skipping whereas B3 gave 24.5% skipping. Although the skipping of myostatin exon 2 was evident, the effect was not sufficient to see a significant change in TA muscle mass (data not shown). From previous work on exon skipping for dystrophin, it is well established that the intramuscular injections of naked unconjugated AOs in undamaged muscles are not very efficient.[25]

High Levels of Myostatin Exon 2 Skipping in C2C12 Cell Culture Following Treatment with a Range of PMOs Designed on the Basis of 2'OMePS Data.

The animal studies above established that exon skipping of the myostatin gene observed after intramuscular injection of 2'OMePS AOs was insufficient to induce change in TA mass. The PMO chemistry has been demonstrated to have very high efficiency in vivo.[33] Therefore, PMOs were designed on the basis of most efficient 2'OMePS AOs (A3, B3, C3, and D3) and initially tested in vitro. PMOs are uncharged chemicals and do not directly interact with the polycationic transfection reagent lipofectamine 2000. In order to enable reasonable transfection efficiency in C2C12 cells, PMOs were hybridized to complementary so-called leash oligonucleotides of natural negatively charged DNA chemistry as previously described.[23,34,35] Nested RT-PCR analysis of mRNA harvested from C2C12 cells treated with leashed-PMO lipoplexes demonstrated that exon skipping was induced by all the PMOs accurate skipping of the targeted exon by both AO chemistries tested here.

Systemic Injection of PMOs Conjugated to Octa-Guanidine Dendrimer Resulted in Myostatin Exon Skipping Associated with a Significant Increase in Muscle Mass and Myofibre Size.

The conjugation of PMO with octa-guanidine dendrimer (so-called Vivo-PMOs) significantly increases the delivery and efficiency of PMO directed against exon 23 of dystrophin compared to unmodified PMO.[25] Therefore, a Vivo-PMO based on the sequence of the previously tested 2'OMePS oligomer, D3, was produced to evaluate systemic intravascular treatment regimes. Mice were treated with 6 mg/kg of Vivo-PMO-D3 by five weekly intravenous injections, and whole body weight and the mass of TA, soleus, and extensor digitorum longus (EDL) muscles were recorded 10 days after the last injection. Among the muscles analyzed in the treated animals the soleus showed a statistically significant change in mass (P=0.034) (FIG. 5a). In accordance with this, high levels of exon skipping of myostatin exon 2 was demonstrated at the transcript level in soleus (79%), whereas a very low level of skipping was observed in EDL muscle (9%) (FIG. 5b). Importantly, the cross-sectional area (CSA) of soleus muscle fibres in treated animals significantly increased (P<0.0001; mean CSA were 254±5 µm2 for control and 333±3 µm2 for PMO-treated animals (n=6) with a significant shift on the distribution of CSA ($\chi^2$=38.34; df=12) (FIG. 5c, d). No change was observed in the CSA of EDL muscle.

Discussion

Although targeting donor splice site, acceptor splice sites and branch point sequences has successfully led to exon exclusion including DMD exon skipping[36-38], some studies have proved that targeting splice sites does not always induce exon skipping and therefore exclusion of an exon from the pre-mRNA[39] These contain some consensus sequences common to many other genes; therefore there lies a possible risk of disrupting the splicing of non-specific genes[40]. Exon splicing enhancers (ESEs) motifs form the binding sites for SR-protein RNA domains and thus help the splicing machinery in exon recognition[41]. It has been shown that intraexonic point mutations usually lead to mRNA level of exon skipping instead of misense or no change in the amino acids[42]. As SR protein binding to ESEs is very crucial for exon exclusion, blocking the ESEs with Antisense oligonucleotides (AOs) would be expected to result in exon skipping. Different software like RESCUE ESE[43,44], ESEFinder[45] and PESX[46] have been widely used to predict possible ESE sites for different SR domains in order to assist in designing AOs[40,47,48]

Different oligonucleotide sequences of two different chemistries to target myostatin exon 2 were designed using these available online tools which showed a promising level of exon skipping. 2'OMePS chemistry was used for the preliminary tissue culture studies because of the advantage of cheap and easy synthesis over some other the PMO chemistry[49,50]. RNA from all the C2C12 cells transfected with twelve different 2'OMePS AO sequences showed skipped myostatin exon 2 as demonstrated by RT-PCR along with the full length product. As myostatin has been established to be a negative regulator of muscle mass growth and differentiation[51-53], a decrease in its level is expected to result in enhanced proliferative capacity of muscle cells[54,55]. Therefore, a colorimetric proliferation assay based on the principle of bioreduction of a tetrazolium compound by viable cells gives a quantitative measure of living cells present in a system[56]. On performing this assay on cells treated with four different AOs (one from each of the four sets based on RT PCR results), it was observed that the cells treated with AO-A3 showed increased proliferation compared to control cells (p<0.01), treatment with AOs B3 and D3 also showed an increased cell proliferation (p<0.05), whereas AO-C3 did not lead to a significant increase in level of proliferation compared to the control cells.

PMO chemistry has high nuclease resistance[57] and it does not induce RNase H-mediated downregulation of the mRNA that it targets[58]. Due to uncharged background, however, PMOs cannot be delivered efficiently across cells using cationic liposomes and needs to be used at very high concentrations[59,60]. Therefore, an anionic single-stranded nucleic acid molecule called 'leash' was annealed to the PMO in order to mediate complex formation of PMO with the cationic transfection reagent[61]. Four different 20-mer 2'OMePS AO sequences were used for design and synthesis of PMOs. PMOs were 30-mers with an overlap of 10 bases between AO-2 and AO-3 of each of the 2'OMePS AO sets, A(1,2,3), B(1,2,3), C(1,2,3) and D(1,2,3). All the PMOs linked to their respective leashes resulted in induction of exon 2 skipping of myostatin mRNA and therefore showed the feasibility of the approach with two different AO chemistries.

A luciferase reporter assay has been used to study the myostatin inhibition effect of myostatin propeptide as well as that of myostatin neutralizing antibody JA16 in terms of a decrease in Smad binding to a TGF-β responsive elements called CAGA boxes[62-64]. A dose-response curve was prepared using different dilutions of recombinant mouse myostatin using human rhabdomyosarcoma cell line, A204 transfected with pGL3-(CAGA)$_{12}$-luc. When supernatant from C2C12 cells treated with PMO-D was assayed on the A204 cells transfected with luciferase reporter containing Smad-binding site (CAGA) and luminescence was recorded, there was found to be a significant decrease (p=0.011) in the relative light units (RLU) after 48 hours in case of supernatant from treated C2C12 cells compared to supernatant from control C2C12 cells. This indicates a decrease in the transcriptional activity of endogenous Smad proteins which are crucial for TGF-β-mediated signal transduction[62] Therefore, inhibition of myostatin by exon skipping results in reduced biological activity related to modulation of myostatin pathway. This study thus confirms the reported results for myostatin blockade using dominant negative ActRIIB in human myoblasts[65] myostatin-neutralizing antibody, JA16[64] and myostatin propeptide[63] showing a decrease in Smad2 transcriptional activity and thus antagonizing biological activity. When the mean RLU values from the reporter assay for PMO-D treated cells were plotted on the myostatin standard curve, there was found to be a decrease in myostatin concentration in treated samples relative to the control cells by 44%. All these results were evident of skipping of myostatin exon 2 in vitro using two different chemistries along with modulation of proliferative capacity as well as alteration of myostatin pathway of AO-treated cells.

Further Discussion

It has been well established that myostatin is a negative regulator of skeletal muscle mass[66] and several approaches have been used to knockdown this factor to induce an increase in skeletal muscle growth.[67] The use of AOs to induce exon skipping and thereby knockdown the expression of myostatin presents several advantages over the other currently used gene therapy approaches. Firstly, there is no risk of uncontrolled insertion into the genome with AOs as in case of virus-mediated approaches.[68] Moreover, with an appropriate dosing regimen, exon skipping levels can be regulated and, if necessary the treatment can be interrupted. Importantly AOs have not been reported to produce any toxic effects or immune response so far in animal models as well as when used in clinical application.[69] Here, the inventors show that AOs of 2'OMePS chemistry, designed using bioinformatics algorithms, resulted in a substantial level of myostatin exon 2 skipping in vitro. Myostatin being an inhibitor of myogenic differentiation, controls the proliferation of myoblasts.[70] Therefore, myostatin knockdown is expected to increase the cell proliferation. The AOs designed were biologically active and induced an increase in C2C12 cell proliferation. The efficacy of knockdown by exon skipping in vivo has proved to be more challenging to establish than in vitro. The efficiency of myostatin skipping was verified by injecting 2'OMePS intramuscularly. The intramuscular treatment of a single muscle induced exon skipping, but did not appear to affect myostatin activity. This is likely to be due to supply of biologically active myostatin to the injected muscle by the bloodstream. Moreover, in a hypothetical clinical approach, the whole body should be treated. For these reasons, the inventors decided to administer the AOs by systemic tail vein injection in further experiments. PMO chemistry was chosen for this experiment due to its better stability compared to the 2'OMePS and also because PMOs have been reported to have a longer effect in vivo.[71] This is particularly important for knocking down proteins like myostatin, which do not have a long half-life like dystrophin. The PMO sequence used for the systemic administration study induced efficient skipping in vitro. It also maps in a region totally conserved between mouse and human myostatin paving the way to test the same PMO for clinical applications in humans. In order to achieve a reasonable effect in undamaged muscles, a PMO conjugated to a delivery moiety has to be used.[72] Vivo-PMO is commercially available and has been reported to be effective in normal healthy mice.[25] By injecting Vivo-PMO, a substantial increase in muscle size and the change of CSA fibre distribution has been obtained, but only in the soleus muscle. The differential response in EDL and soleus may be due in part to a greater amount of ActRIIb being expressed on the surface of EDL muscle, or because the intrinsic level of myostatin is greater in fast (myosin type IIb positive) myofibres.[4,6] Alternatively, it can be speculated that the dosing regimen used, which has been reported to be optimal for Vivo-PMO for exon skipping of dystrophin gene,[25] does not achieve sufficient skipping of myostatin gene in EDL. In the case of dystrophin skipping, the half-life of dystrophin protein and mRNA is extremely long and therefore relatively smaller dosage of AO gives more sustained exon skipping.[73] However, in myostatin skipping, it is perhaps likely that more frequent redosing is required, to have a more sustained presence of AOs. This may explain the transient and weak effect in terms of whole body weight change that was observed in vivo. Interestingly, only soleus muscle showed a significant increase in weight and CSA fibre distribution. This is in compliance with some previously published data showing that soleus is the most affected muscle following a systemic approach to knockdown myostatin.[4] The results represent a proof-of-principle that myostatin knockdown can be obtained by skipping an exon from the transcript by using AOs.

Example 2

The 30-mer PMO AOs tested above (Mstn-A to Mstn-D) were designed to target the myostatin gene in mice. Therefore, these Mstn-A to Mstn-D sequences correspond (are complementary to) to the Genbank mouse myostatin cDNA/mRNA gene sequence. The corresponding sequences complementary to the Genbank human myostatin sequences are as follows with differences between the Genbank mouse and human underlined:

```
                                        (SEQ ID NO: 32)
Hum Mstn A:    TCTCGACGGGTCTCAAATATATCCATAGTT (SEQ ID NO: 33)
Hum Mstn B:    TGTACCGTCTTTCATAGGTTTGATGAGTCT (SEQ ID NO: 34)
Hum Mstn C:    CCTGGGTTCATGTCAAGTTTCAGAGATCGG (SEQ ID NO: 35)
Hum Mstn D:    CAGCCCATCTTCTCCTGGTCCTGGGAAGGT
```

The skipping efficiency of these AOs can be tested by transfection (leashed or unleashed: concentration between 50 and 500 nM) into cultured human myoblast cells (eg using a transfection reagent such as Lipofectamine2000), and evaluation of skipped and unskipped mRNAs by electrophoretic densitometric analysis of RTPCR reaction products.

REFERENCES

1. McPherron, A C, Lawler, A M and Lee, S J (1997). Regulation of skeletal muscle mass in mice by a new TGF-β superfamily member. *Nature* 387: 83-90.
2. Schuelke, M, Wagner, K R, Stolz, L E, Hübner, C, Riebel, T, Kömen, W et al. 2004). Myostatin mutation associated with gross muscle hypertrophy in a child. *N Engl J Med* 350: 2682-2688.
3. Bogdanovich, S, Perkins, K J, Krag, T O, Whittemore, L A and Khurana, T S (2005). Myostatin propeptide-mediated amelioration of dystrophic pathophysiology. *FASEB J* 19: 543-549.
4. Foster, K, Graham, I R, Otto, A, Foster, H, Trollet, C, Yaworsky, P J et al. (2009). Adeno-associated virus-8-mediated intravenous transfer of myostatin propeptide leads to systemic functional improvements of slow but not fast muscle. *Rejuvenation Res* 12: 85-94.
5. Qiao, C, Li, J, Jiang, J, Zhu, X, Wang, B, Li, J et al. (2008). Myostatin propeptide gene delivery by adeno-associated virus serotype 8 vectors enhances muscle growth and ameliorates dystrophic phenotypes in mdx mice. *Hum Gene Ther* 19: 241-254.
6. Foster, K W (2009). Eye evolution: two eyes can be better than one. *Curr Biol* 19: R208-R210.
7. Haidet, A M, Rizo, L, Handy, C, Umapathi, P, Eagle, A, Shilling, C et al. (2008). Long-term enhancement of skeletal muscle mass and strength by single gene administration of myostatin inhibitors. *Proc Natl Acad Sci USA* 105: 4318-4322.
8. Wagner, K R, Fleckenstein, J L, Amato, A A, Barohn, R J, Bushby, K, Escolar, D M et al. (2008). A phase I/IItrial of MYO-029 in adult subjects with muscular dystrophy. *Ann Neurol* 63: 561-571.
9. Whittemore, L A, Song, K, Li, X, Aghajanian, J, Davies, M, Girgenrath, S et al. (2003). Inhibition of myostatin in adult mice increases skeletal muscle mass and strength. *Biochem Biophys Res Commun* 300: 965-971.
10. Yang, Z, Zhang, J, Cong, H, Huang, Z, Sun, L, Liu, C et al. (2008). A retrovirus-based system to stably silence GDF-8 expression and enhance myogenic differentiation in human rhabdomyosarcoma cells. *J Gene Med* 10: 825-833.
11. Dumonceaux, J, Marie, S, Beley, C, Trollet, C, Vignaud, A, Ferry, A et al. (2010). Combination of myostatin pathway interference and dystrophin rescue enhances tetanic and specific force in dystrophic mdx mice. *Mol Ther* 18: 881-887.
12. Weinstein, S and Peer, D (2010). RNAi nanomedicines: challenges and opportunities within the immune system. *Nanotechnology* 21: 232001.
13. Hausen, P and Stein, H (1970). Ribonuclease H. An enzyme degrading the RNA moiety of DNA-RNA hybrids. *Eur J Biochem* 14: 278-283.
14. Zamecnik, P C and Stephenson, M L (1978). Inhibition of Rous sarcoma virus replication and cell transformation by a specific oligodeoxynucleotide. *Proc Natl Acad Sci USA* 75: 280-284.
15. Dominski, Z and Kole, R (1993). Restoration of correct splicing in thalassemic premRNA by antisense oligonucleotides. *Proc Natl Acad Sci USA* 90: 8673-8677.
16. Friedman, K J, Kole, J, Cohn, J A, Knowles, M R, Silverman, L M and Kole, R (1999). Correction of aberrant splicing of the cystic fibrosis transmembrane conductance regulator (CFTR) gene by antisense oligonucleotides. *J Biol Chem* 274: 36193-36199.
17. Sierakowska, H, Sambade, M J, Agrawal, S and Kole, R (1996). Repair of thalassemic human β-globin mRNA in mammalian cells by antisense oligonucleotides. *Proc Natl Acad Sci USA* 93: 12840-12844.
18. Dunckley, M G, Manoharan, M, Villiet, P, Eperon, I C and Dickson, G (1998). Modification of splicing in the dystrophin gene in cultured Mdx muscle cells by antisense oligoribonucleotides. *Hum Mol Genet* 7: 1083-1090.
19. Cartegni, L, Chew, S L and Krainer, A R (2002). Listening to silence and understanding nonsense: exonic mutations that affect splicing. *Nat Rev Genet* 3: 285-298.
20. Kinali, M, Arechavala-Gomeza, V, Feng, L, Cirak, S, Hunt, D, Adkin, C et al. (2009). Local restoration of dystrophin expression with the morpholino oligomer AVI-4658 in Duchenne muscular dystrophy: a single-blind, placebo-controlled, dose-escalation, proof-of-concept study. *Lancet Neurol* 8: 918-928.
21. van Deutekom, J C, Janson, A A, Ginjaar, I B, Frankhuizen, W S, Aartsma-Rus, A, Bremmer-Bout, M et al. (2007). Local dystrophin restoration with antisense oligonucleotide PRO051. *N Engl J Med* 357: 2677-2686.
22. Hudziak, R M, Barofsky, E, Barofsky, D F, Weller, D L, Huang, S B and Weller, D D (1996). Resistance of morpholino phosphorodiamidate oligomers to enzymatic degradation. *Antisense Nucleic Acid Drug Dev* 6: 267-272.
23. Popplewell, L J, Trollet, C, Dickson, G and Graham, I R (2009). Design of phosphorodiamidate morpholino oligomers (PMOs) for the induction of exon skipping of the human DMD gene. *Mol Ther* 17: 554-561.
24. Gebski, B L, Errington, S J, Johnsen, R D, Fletcher, S and Wilton, S D (2005). Terminal antisense oligonucleotide modifications can enhance induced exon skipping. *Neuromuscul Disord* 15: 622-629.
25. Wu, B, Li, Y, Morcos, P A, Doran, T J, Lu, P and Lu, Q L (2009). Octa-guanidine morpholino restores dystrophin expression in cardiac and skeletal muscles and ameliorates pathology in dystrophic mdx mice. *Mol Ther* 17: 864-871.

26. Jearawiriyapaisarn, N., Moulton, H. M., Sazani, P., Kole, R. & Willis, M. S. (2010). Long-term improvement in mdx cardiomyopathy after therapy with peptide-conjugated morpholino oligomers. *Cardiovasc Res* 85, 444-453
27. Cartegni, L, Wang, J, Zhu, Z, Zhang, M Q and Krainer, A R (2003). ESEfinder: A web resource to identify exonic splicing enhancers. *Nucleic Acids Res* 31: 3568-3571.
28. Smith, P J, Zhang, C, Wang, J, Chew, S L, Zhang, M Q and Krainer, A R (2006). An increased specificity score matrix for the prediction of SF2/ASF-specific exonic splicing enhancers. *Hum Mol Genet* 15: 2490-2508.
29. Zhang, X H and Chasin, L A (2004). Computational definition of sequence motifs governing constitutive exon splicing. *Genes Dev* 18: 1241-1250.
30. Zhang, X H, Leslie, C S and Chasin, L A (2005). Computational searches for splicing signals. *Methods* 37: 292-305.
31. Fairbrother, W G, Yeh, R F, Sharp, P A and Burge, C B (2002). Predictive identification of exonic splicing enhancers in human genes. *Science* 297: 1007-1013.
32. Spitali, P, Heemskerk, H, Vossen, R H, Ferlini, A, den Dunnen, J T, 't Hoen, P A et al. (2010). Accurate quantification of dystrophin mRNA and exon skipping levels in Duchenne Muscular Dystrophy. *Lab Invest* 90: 1396-1402.
33. Alter, J, Lou, F, Rabinowitz, A, Yin, H, Rosenfeld, J, Wilton, S D et al. (2006). Systemic delivery of morpholino oligonucleotide restores dystrophin expression bodywide and improves dystrophic pathology. *Nat Med* 12: 175-177.
34. Popplewell, L J, Adkin, C, Arechavala-Gomeza, V, Aartsma-Rus, A, de Winter, C L, Wilton, S D et al. (2010). Comparative analysis of antisense oligonucleotide sequences targeting exon 53 of the human DMD gene: Implications for future clinical trials. *Neuromuscul Disord* 20: 102-110.
35. Gebski, B L, Mann, C J, Fletcher, S and Wilton, S D (2003). Morpholino antisense oligonucleotide induced dystrophin exon 23 skipping in mdx mouse muscle. *Hum Mol Genet* 12: 1801-1811.
36. Graham, I. R., Hill, V. J., Manoharan, M., Inamati, G. B. & Dickson, G. (2004). Towards a therapeutic inhibition of dystrophin exon 23 splicing in mdx mouse muscle induced by antisense oligoribonucleotides (splicomers): target sequence optimisation using oligonucleotide arrays. *Journal of Gene Medicine* 6: 1149-1158.
37. Wilton, S. D. & Fletcher, S. (2005). Antisense oligonucleotides in the treatment of Duchenne muscular dystrophy: Where are we now? *Neuromuscul Disord* 15: 399-402.
38. Wilton, S. D., Mann, C. J., Honeyman, K., McClorey, G. & Fletcher, S. (2002). Improved antisense oligonucleotide induced exon skipping in the mdx mouse model of muscular dystrophy. *Journal of Gene Medicine* 4: 644-654.
39. Wilton, S. D., McClorey, G., Moulton, H. M., Iversen, P. L. & Fletcher, S. (2006). Antisense oligonucleotide-induced exon skipping restores dystrophin expression in vitro in a canine model of DMD. *Gene Therapy* 13: 1373-1381
40. Aartsma-Rus, A., Heemskerk, H., de Winter, C., van Putten, M., Janson, A., Verschuuren, J., den Dunnen, J., van Deutekom, J. & van Ommen, G. J. (2009). Antisense-Mediated Exon Skipping for Duchenne Muscular Dystrophy. *Human Gene Therapy* 20: 660-661.
41. Stojdl, D. F. & Bell, J. C. (1999). S R protein kinases: the splice of life. *Biochemistry and Cell Biology-Biochimie Et Biologie Cellulaire* 77: 293-298.
42. Krainer, A. R. & Cartegni, L. (2002). Disruption of an SF2/ASF-dependent exonic splicing enhancer in SMN2 causes spinal muscular atrophy in the absence of SMN1. *Nature Genetics* 30, 377-384.
43. Burge, C. B., Fairbrother, W. G., Yeh, R. F. & Sharp, P. A. (2002). Predictive identification of exonic splicing enhancers in human genes. *Science* 297: 1007-1013.
44. Burge, C. B., Fairbrother, W. G., Yeo, G. W., Yeh, R., Goldstein, P., Mawson, M. & Sharp, P. A. (2004). RESCUE-ESE identifies candidate exonic splicing enhancers in vertebrate exons. *Nucleic Acids Research* 32: W187-W190.
45. Krainer, A. R., Cartegni, L., Wang, J. H., Zhu, Z. W. & Zhang, M. Q. (2003). ESEfinder: a web resource to identify exonic splicing enhancers. *Nucleic Acids Research* 31: 3568-3571.
46. Chasin, L. A. & Zhang, X. H. F. (2004). Computational definition of sequence motifs governing constitutive exon splicing. *Genes & Development* 18, 1241-1250
47. van Deutekom, J., Aartsma-Rus, A., Bremmer-Bout, M., Janson, A., den Dunnen, J. & van Ommen, G. J. (2002). Antisense-mediated exon skipping as a gene correction therapy for Duchenne muscular dystrophy. *Journal of the Neurological Sciences* 199: S75-S76.
48. van Deutekom, J. C. & van Ommen, G. J. (2003). Advances in Duchenne muscular dystrophy gene therapy. *Nat Rev Genet* 4: 774-783
49. Agrawal, S. (1999). Importance of nucleotide sequence and chemical modifications of antisense oligonucleotides. *Biochim Biophys Acta* 1489: 53-68.
50. Sazani, P., Vacek, M. M. & Kole, R. (2002). Short-term and long-term modulation of gene expression by antisense therapeutics. *Curr Opin Biotechnol* 13: 468-472.
51. Grobet, L., Martin, L. J., Poncelet, D., Pirottin, D., Brouwers, B., Riquet, J., Schoeberlein, A., Dunner, S., Menissier, F., Massabanda, J., Fries, R., Hanset, R. & Georges, M. (1997). A deletion in the bovine myostatin gene causes the double-muscled phenotype in cattle. *Nat Genet* 17: 71-74.
52. McPherron, A. C. & Lee, S. J. (1997). Double muscling in cattle due to mutations in the myostatin gene. *Proc Natl Acad Sci USA* 94: 12457-12461.
53. Szabo, G., Dallmann, G., Muller, G., Patthy, L., Soller, M. & Varga, L. (1998). A deletion in the myostatin gene causes the compact (Cmpt) hypermuscular mutation in mice. *Mamm Genome* 9: 671-672.
54. Thomas, M., Langley, B., Berry, C., Sharma, M., Kirk, S., Bass, J. & Kambadur, R. (2000). Myostatin, a negative regulator of muscle growth, functions by inhibiting myoblast proliferation. *J Biol Chem* 275: 40235-40243.
55. Zhu, X., Hadhazy, M., Wehling, M., Tidball, J. G. & McNally, E. M. (2000). Dominant negative myostatin produces hypertrophy without hyperplasia in muscle. *FEBS Lett* 474: 71-75.
56. Berridge, M. V. & Tan, A. S. (1993). Characterization of the cellular reduction of 3-(4,5-dimethylthiazol-2-yl)-2,5-diphenyltetrazolium bromide (MTT): subcellular localization, substrate dependence, and involvement of mitochondrial electron transport in MTT reduction. *Arch Biochem Biophys* 303: 474-482.
57. Summerton, J., Stein, D., Huang, S. B., Matthews, P., Weller, D. & Partridge, M. (1997). Morpholino and phosphorothioate antisense oligomers compared in cell-free and in-cell systems. *Antisense Nucleic Acid Drug Dev* 7: 63-70.
58. Hudziak, R. M., Barofsky, E., Barofsky, D. F., Weller, D. L., Huang, S. B. & Weller, D. D. (1996). Resistance of morpholino phosphorodiamidate oligomers to enzymatic degradation. *Antisense Nucleic Acid Drug Dev* 6: 267-272.
59. Sazani, P., Kang, S. H., Maier, M. A., Wei, C., Dillman, J., Summerton, J., Manoharan, M. & Kole, R. (2001). Nuclear antisense effects of neutral, anionic and cationic oligonucleotide analogs. *Nucleic Acids Res* 29: 3965-3974.
60. Suwanmanee, T., Sierakowska, H., Lacerra, G., Svasti, S., Kirby, S., Walsh, C. E., Fucharoen, S. & Kole, R. (2002). Restoration of human beta-globin gene expression in murine and human IVS2-654 thalassemic erythroid cells by free uptake of antisense oligonucleotides. *Mol Pharmacol* 62: 545-553.
61. Gebski, B. L., Mann, C. J., Fletcher, S. & Wilton, S. D. (2003). Morpholino antisense oligonucleotide induced dystrophin exon 23 skipping in mdx mouse muscle. *Hum Mol Genet* 12: 1801-1811.
62. Dennler, S., Itoh, S., Vivien, D., ten Dijke, P., Huet, S. & Gauthier, J. M. (1998). Direct binding of Smad3 and Smad4 to critical TGF beta-inducible elements in the promoter of human plasminogen activator inhibitor-type 1 gene. *EMBO J* 17: 3091 3100.
63. Thies, R. S., Chen, T., Davies, M. V., Tomkinson, K. N., Pearson, A. A., Shakey, Q. A. & Wolfman, N. M. (2001). GDF-8 propeptide binds to GDF-8 and antagonizes biological activity by inhibiting GDF-8 receptor binding. *Growth Factors* 18:251-259.
64. Whittemore, L. A., Song, K., Li, X., Aghajanian, J., Davies, M., Girgenrath, S., Hill, J. J., Jalenak, M., Kelley, P., Knight, A., Maylor, R., O'Hara, D., Pearson, A., Quazi, A., Ryerson, S., Tan, X. Y., Tomkinson, K. N., Veldman, G. M., Widom, A., Wright, J. F., Wudyka, S., Zhao, L. & Wolfman, N. M. (2003). Inhibition of myostatin in adult mice increases skeletal muscle mass and strength. *Biochem Biophys Res Commun* 300, 965-971.
65. Fakhfakh, R., Michaud, A. & Tremblay, J. P. (2011). Blocking the myostatin signal with a dominant negative receptor improves the success of human myoblast transplantation in dystrophic mice. *Mol Ther* 19: 204-210.
66. Carnac, G, Ricaud, S, Vernus, B and Bonnieu, A (2006). Myostatin: biology and clinical relevance. *Mini Rev Med Chem* 6: 765-770.
67. Patel, K and Amthor, H (2005). The function of Myostatin and strategies of Myostatin blockade-new hope for therapies aimed at promoting growth of skeletal muscle. *Neuromuscul Disord* 15: 117-126.
68. Amantana, A and Iversen, P L (2005). Pharmacokinetics and biodistribution of phosphorodiamidate morpholino antisense oligomers. *Curr Opin Pharmacol* 5: 550-555.
69. Arora, V, Devi, G R and Iversen, P L (2004). Neutrally charged phosphorodiamidate morpholino antisense oligomers: uptake, efficacy and pharmacokinetics. *Curr Pharm Biotechnol* 5: 431-439.
70. Langley, B, Thomas, M, Bishop, A, Sharma, M, Gilmour, S and Kambadur, R (2002). Myostatin inhibits myoblast differentiation by down-regulating MyoD expression. *J Biol Chem* 277: 49831-49840.
71. Iversen, P L (2001). Phosphorodiamidate morpholino oligomers: favorable properties for sequence-specific gene inactivation. *Curr Opin Mol Ther* 3: 235-238.
72. Morcos, P A, Li, Y and Jiang, S (2008). Vivo-Morpholinos: a non-peptide transporter delivers Morpholinos into a wide array of mouse tissues. *BioTechniques* 45: 613-4, 616, 618 passim.
73. Ghahramani Seno, M M, Graham, I R, Athanasopoulos, T, Trollet, C, Pohlschmidt, M, Crompton, M R et al. (2008). RNAi-mediated knockdown of dystrophin expression in adult mice does not lead to overt muscular dystrophy pathology. *Hum Mol Genet* 17: 2622-2632.
74 Paola Rimessi P, et al. Cationic PMMA Nanoparticles Bind and Deliver Antisense Oligoribonucleotides Allowing Restoration of Dystrophin Expression in the mdx Mouse. *Molecular Therapy* (2009) 17 5, 820-827 doi: 10.1038/mt.2009.8)
75. Cory, A H, Owen, T C, Barltrop, J A and Cory, J G (1991). Use of an aqueous soluble tetrazolium/formazan assay for cell growth assays in culture. *Cancer Commun* 3: 207-212.

The invention claimed is:

1. An oligomer for inducing exon skipping during processing of myostatin pre-mRNA, the oligomer comprising at least 20 contiguous bases of a base sequence selected from:

1) XGXACCGXCXXXCAXGGGXXXGAXGAGXCX; (SEQ ID NO. 6)

2) CCXGGGCXCAXGXCAAGXXXCAGAGAXCGG; (SEQ ID NO. 7)

3) XCCACAGXXGGGCXXXXACX; (SEQ ID NO. 8)

4) XGAXGAGXCXCAGGAXXXGC; (SEQ ID NO. 11)

5) XXCAXGGGXXXGAXGAGXCX; (SEQ ID NO. 12)

6) CAGAGAXCGGAXXCCAGXAX; (SEQ ID NO. 14)
and

7) XGXCAAGXXXCAGAGAXCGG, (SEQ ID NO. 15)

wherein X is T or U and the oligomer's sequence can vary from the above sequence at up to two base positions, and wherein the oligomer can bind to a target site in the myostatin pre-mRNA to cause exon skipping, wherein the oligomer is a phosphorodiamidate morpholino oligonucleotide (PMO) or a phosphorothioate-linked 2'-O-methyl oligonucleotide (2'OMePS).

2. The oligomer of claim 1, wherein the oligomer causes an exon skipping rate of at least 40%.

3. The oligomer of claim 1, wherein the oligomer causes an exon skipping rate of at least 90%.

4. The oligomer of claim 1, wherein the oligomer is a phosphorodiamidate morpholino oligonucleotide (PMO).

5. The oligomer of claim 1, wherein the oligomer is between 20 and 40 bases in length.

6. The oligomer of claim 1, wherein the oligomer is about 30 bases in length.

7. The oligomer of claim 1, wherein the base sequence is selected from SEQ ID NOS. 6-8.

8. The oligomer of claim 1, wherein the base sequence is selected from SEQ ID NOS. 11, 12, 14, and 15.

9. The oligomer of claim 1, wherein the oligomer is conjugated to or complexed with a distinct chemical entity.

10. A vector for inducing exon skipping during processing of myostatin pre-mRNA, the vector encoding an oligomer of claim 1, wherein when the vector is introduced into a cell, the oligomer is expressed.

11. A method of inducing exon skipping during processing of myostatin pre-mRNA in a patient, the method comprising administering a therapeutically effective amount of the oligomer of claim 1 or the vector of claim 10 to the patient such that exon skipping during processing of myostatin pre-mRNA is induced.

12. The method of claim 11, wherein the method is for increasing or maintaining muscle mass, or slowing degeneration of muscle mass in the patient.

13. The method of claim 11, wherein the method is for ameliorating muscle wasting conditions.

14. The method of claim 11, wherein the method is for ameliorating a muscular dystrophy such as Becker's muscular dystrophy, congenital muscular dystrophy, Duchenne muscular dystrophy, distal muscular dystrophy, Emery-Dreifuss muscular dystrophy, facioscapulohumeral muscular dystrophy (FSHD), limb-girdle muscular dystrophy, myotonic muscular dystrophy and oculopharyngeal muscular dystrophy.

15. The method of claim 11, wherein the method is for ameliorating Duchenne muscular dystrophy.

16. The method of claim 15, wherein the exon skipping occurs in the dystrophin gene and which ameliorates Duchenne muscular dystrophy.

17. The oligomer of claim 2, wherein the exon skipping rate is measured in C2C12 mouse myoblast cells after treatment with an oligomer by comparing gene expression levels of the exon in the cells to total gene expression levels in the cells.

18. The oligomer of claim 3, wherein the exon skipping rate is measured in C2C12 mouse myoblast cells after treatment with an oligomer by comparing gene expression levels of the exon in the cells to total gene expression levels in the cells.

* * * * *

SEQUENCE LISTING

<160> NUMBER OF SEQ ID NOS: 36

<210> SEQ ID NO 1
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(30)
<223> OTHER INFORMATION: N=U or T

<400> SEQUENCE: 1
ncncgacggg ncncaaanan anccanagnn                30

<210> SEQ ID NO 2
<211> LENGTH: 30
<212> TYPE: DNA
<213> ORGANISM: Artificial Sequence
<220> FEATURE:
<223> OTHER INFORMATION: synthetic sequence
<220> FEATURE:

<221> NAME/KEY: misc_feature
<222> LOCATION: (1)...(30)
<223> OTHER INFORMATION: N=U or T

<400> SEQUENCE: 2
ngnaccgncn nncanaggnn ngangagncn                                              30

<210> SEQ ID NO 3
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(30)
<223> OTHER INFORMATION: N=U or T

<400> SEQUENCE: 3
ccngggnnca ngncaagnnn cagagancgg                                              30

<210> SEQ ID NO 4
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(30)
<223> OTHER INFORMATION: N=U or T

<400> SEQUENCE: 4
cagcccancn ncnccnggnc cnggaaggn                                               30

<210> SEQ ID NO 5
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(30)
<223> OTHER INFORMATION: N=U or T

<400> SEQUENCE: 5
ncnngacggg ncngaganan anccacagnn                                              30

<210> SEQ ID NO 6
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(30)
<223> OTHER INFORMATION: N=U or T

<400> SEQUENCE: 6
ngnaccgncn nncangggnn ngangagncn                                              30

<210> SEQ ID NO 7
<211> LENGTH: 30
<212> TYPE: DNA
<213> ORGANISM: Artificial Sequence
<220> FEATURE:
<223> OTHER INFORMATION: synthetic sequence

```
<220> FEATURE:
<221> NAME/KEY: misc_feature
<222> LOCATION: (1)...(30)
<223> OTHER INFORMATION: N=U or T

<400> SEQUENCE: 7
ccngggcnca ngncaagnnn cagagancgg                                          30

<210> SEQ ID NO 8
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 8
nccacagnng ggcnnnnacn                                                     20

<210> SEQ ID NO 9
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 9
ncngaganan anccacagnn                                                     20

<210> SEQ ID NO 10
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 10
ncnngacggg ncngaganan                                                     20

<210> SEQ ID NO 11
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 11
ngangagncn caggannngc                                                     20

<210> SEQ ID NO 12
<211> LENGTH: 20
<212> TYPE: DNA
<213> ORGANISM: Artificial Sequence
<220> FEATURE:
```

```
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 12
nncangggnn ngangagncn                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 13
nngnaccgnc nnncangggn                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 14
cagagancgg anncagnan                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 15
ngncaagnnn cagagancgg                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 16
ccngggcnca ngncaagnnn                                              20

<210> SEQ ID NO 17
<211> LENGTH: 20
<212> TYPE: DNA
<213> ORGANISM: Artificial Sequence
```

```
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 17
cngggaaggn nacagcaaga                                             20

<210> SEQ ID NO 18
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 18
ncnccnggnc cngggaaggn                                             20

<210> SEQ ID NO 19
<211> LENGTH: 20
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)...(20)
<223> OTHER INFORMATION: N=U or T

<400> SEQUENCE: 19
cagcccancn ncnccnggnc                                             20

<210> SEQ ID NO 20
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 20
tccacagttg ggcttttact                                             20

<210> SEQ ID NO 21
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 21
tctgagatat atccacagtt                                             20

<210> SEQ ID NO 22
<211> LENGTH: 20
<212> TYPE: DNA
<213> ORGANISM: Homo sapiens
<220> FEATURE:
<221> NAME/KEY: exon
<222> LOCATION: (1)...(20)
```

```
<223> OTHER INFORMATION: myostatin exon 2

<400> SEQUENCE: 22
tcttgacggg tctgagatat                                           20

<210> SEQ ID NO 23
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 23
tgatgagtct caggatttgc                                           20

<210> SEQ ID NO 24
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 24
ttcatgggtt tgatgagtct                                           20

<210> SEQ ID NO 25
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 25
ttgtaccgtc tttcatgggt                                           20

<210> SEQ ID NO 26
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 26
cagagatcgg attccagtat                                           20

<210> SEQ ID NO 27
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 27
tgtcaagttt cagagatcgg                                           20

<210> SEQ ID NO 28
<211> LENGTH: 20
```

```
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 28
cctgggctca tgtcaagttt                                               20

<210> SEQ ID NO 29
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 29
ctgggaaggt tacagcaaga                                               20

<210> SEQ ID NO 30
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 30
tctcctggtc ctgggaaggt                                               20

<210> SEQ ID NO 31
<211> LENGTH: 20
<212> TYPE: DNA
<213> ORGANISM: Homo sapiens
<220> FEATURE:
<221> NAME/KEY: exon
<222> LOCATION: (1)...(20)
<223> OTHER INFORMATION: myostatin exon 2

<400> SEQUENCE: 31
cagcccatct tctcctggtc                                               20

<210> SEQ ID NO 32
<211> LENGTH: 30
<212> TYPE: DNA
<213> ORGANISM: Homo sapiens
<220> FEATURE:
<221> NAME/KEY: exon
<222> LOCATION: (1)...(30)
<223> OTHER INFORMATION: myostatin exon 2

<400> SEQUENCE: 32
tcttgacggg tctgagatat atccacagtt                                    30

<210> SEQ ID NO 33
<211> LENGTH: 30
<212> TYPE: DNA
<213> ORGANISM: Homo sapiens
<220> FEATURE:
<221> NAME/KEY: exon
<222> LOCATION: (1)...(30)
<223> OTHER INFORMATION: myostatin exon 2

<400> SEQUENCE: 33
```

```
tgtaccgtct ttcatgggtt tgatgagtct                                              30

<210> SEQ ID NO 34
<211> LENGTH: 30
<212> TYPE: DNA
<213> ORGANISM: Homo sapiens
<220> FEATURE:
<221> NAME/KEY: exon
<222> LOCATION: (1)...(30)
<223> OTHER INFORMATION: myostatin exon 2

<400> SEQUENCE: 34
cctgggctca tgtcaagttt cagagatcgg                                              30

<210> SEQ ID NO 35
<211> LENGTH: 30
<212> TYPE: DNA
<213> ORGANISM: Homo sapiens
<220> FEATURE:
<221> NAME/KEY: exon
<222> LOCATION: (1)...(30)
<223> OTHER INFORMATION: myostatin exon 2

<400> SEQUENCE: 35
cagcccatct tctcctggtc ctgggaaggt                                              30

<210> SEQ ID NO 36
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (1)...(14)
<223> OTHER INFORMATION: A=beta-alanine
<220> FEATURE:
<221> NAME/KEY: VARIANT
<222> LOCATION: (0)...(0)
<223> OTHER INFORMATION: Xaa = Any Amino Acid

<400> SEQUENCE: 36

Arg Xaa Arg Arg Ala Arg Arg Xaa Arg Arg Ala Arg Xaa Ala
1               5                   10
```